United States Patent
Han

(10) Patent No.: US 12,030,929 B2
(45) Date of Patent: Jul. 9, 2024

(54) FUSOBACTERIUM NUCLEATUM AMYLOID-LIKE FadA FOR DIAGNOSIS AND TREATMENT OF FN-MEDIATED PATHOGENESIS

(71) Applicant: The Trustees of Columbia University in the City of New York, New York, NY (US)

(72) Inventor: Yiping Han, Paramus, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/457,239

(22) Filed: Aug. 28, 2023

(65) Prior Publication Data

US 2024/0083985 A1    Mar. 14, 2024

Related U.S. Application Data

(63) Continuation of application No. PCT/US2022/023479, filed on Apr. 5, 2022.

(60) Provisional application No. 63/172,971, filed on Apr. 9, 2021.

(51) Int. Cl.
  *C07K 16/12* (2006.01)
(52) U.S. Cl.
  CPC ...... *C07K 16/1203* (2013.01); *C07K 2317/24* (2013.01); *C07K 2317/565* (2013.01)
(58) Field of Classification Search
  None
  See application file for complete search history.

(56) References Cited

U.S. PATENT DOCUMENTS

| | | | |
|---|---|---|---|
| 9,670,548 B2 * | 6/2017 | Han | C12Q 1/689 |
| 2018/0110795 A1 | 4/2018 | Frias-Lopez | |
| 2019/0153471 A1 | 5/2019 | Paul et al. | |

FOREIGN PATENT DOCUMENTS

| | | |
|---|---|---|
| CN | 108351357 A | 7/2018 |
| CN | 112512577 A | 3/2021 |
| WO | WO 2017/192589 A1 | 11/2017 |
| WO | WO 2020/236792 A1 | 11/2020 |

OTHER PUBLICATIONS

Honig. "Trial of Solanezumab for Mild Dementia Due to Alzheimer's Disease" 321-330. The new england journal of medicine . . . Jan. 2018; abstract; p. 322, col. 1, paragraph 1; DOI; 10.1056/NEJMoa1705971.

International Search Report dated Sep. 12, 2022 in connection with PCT International Application No. PCT/US22/23479.

Notification of Transmittal of the International Search Report and the Written Opinion of the International Searching Authority, or the Declaration dated Sep. 12, 2022 in connection with PCT International Application No. PCT/US22/23479.

Written Opinion of the International Searching Authority dated Sep. 12, 2022 in connection with PCT International Application No. PCT/US22/23479.

* cited by examiner

*Primary Examiner* — Meera Natarajan
(74) *Attorney, Agent, or Firm* — Amster, Rothstein & Ebenstein LLP

(57) ABSTRACT

Anti-Fn amyloid-like FadA antibodies and compositions are provided and methods of treating cancers, including pancreatic and colorectal, and periodontal diseases. Methods include preventing, reducing development, or treating disease in a subject in a subject in need thereof comprising administering to the subject a therapeutically effective amount of an agent which inhibits or blocks an amyloid-like FadA secreted from *Fusobacterium nucleatum* (Fn).

16 Claims, 15 Drawing Sheets

Specification includes a Sequence Listing.

2A
```
                                                   -18 MKKFLLLA VLAVSASAPA
  1 ATDAASLVGE LQALDAEYQN LANQEEARFN EERAQADAAR QALAQNEQVY NELSQRAQRL
    QAEANTRFYK SQYQELASKY EDALKKLEAE MEQQKAVISD FEKIQALRAG N 111
```
2B
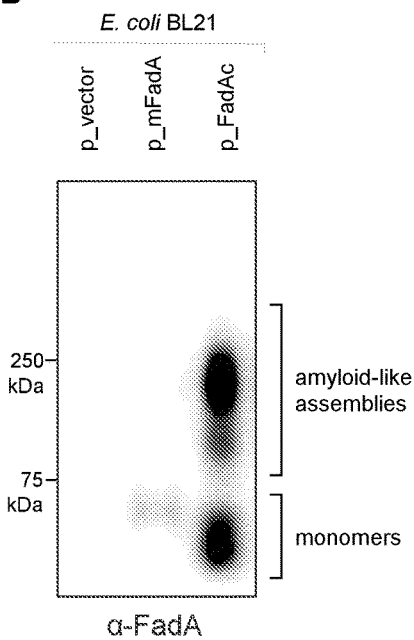
2C
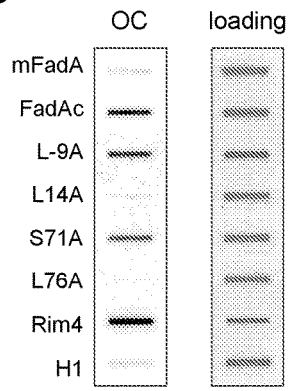
2D
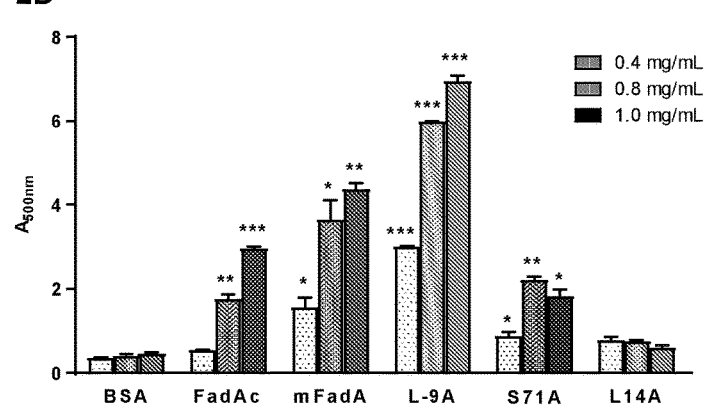
2E
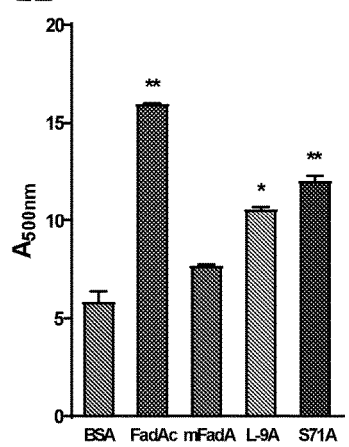
2F
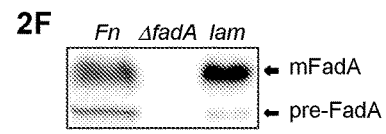
2G
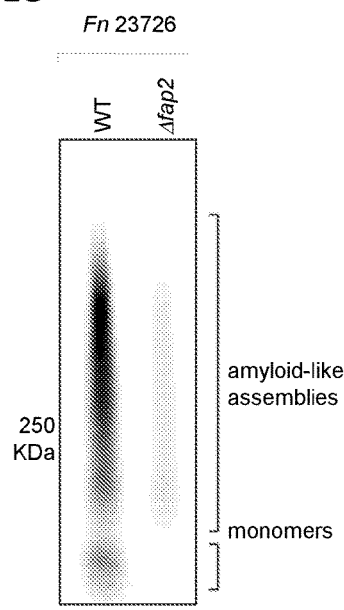
Fig. 2A-2G 5A
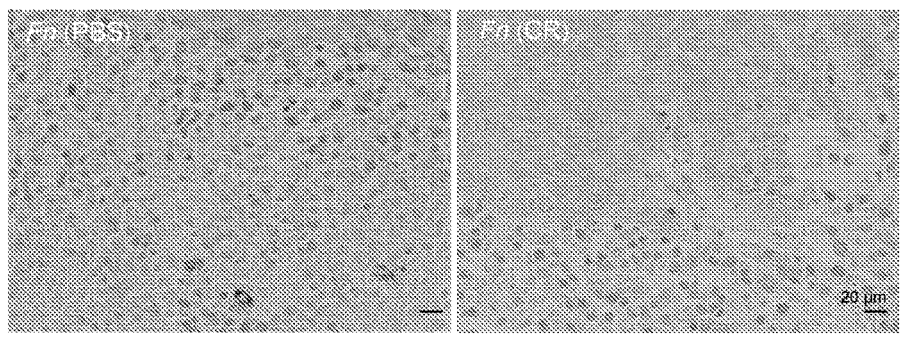
5B
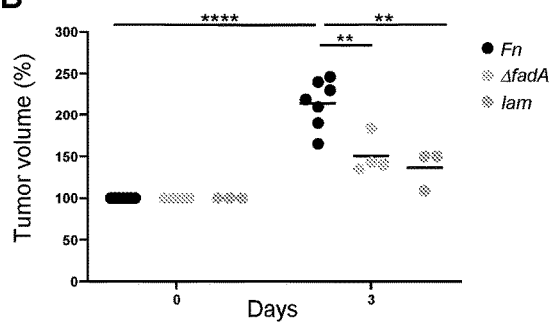
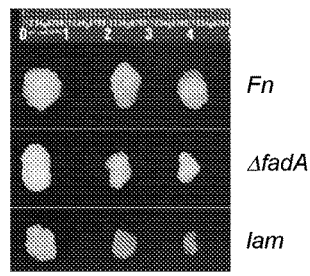
5C
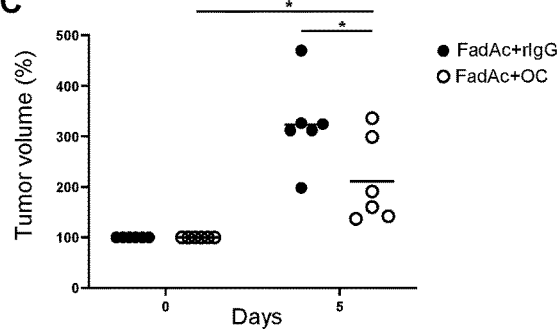
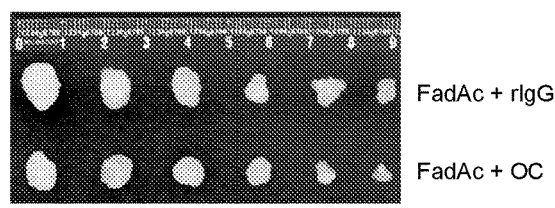
5D
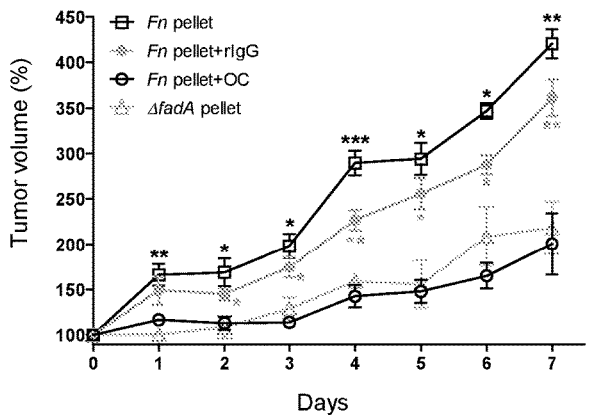
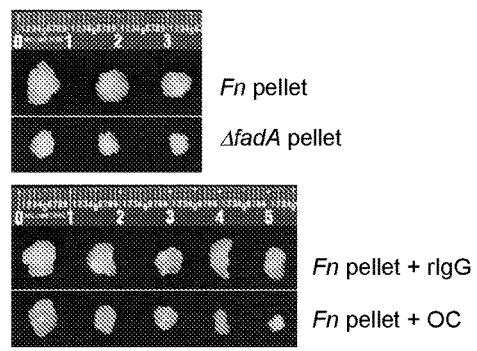
Fig. 5A-5D

10A

10B

48 hr

|       | final OD | CFU      |
|-------|----------|----------|
| 12230 | 0.844    | 1.25E+07 |
| 10 CR | 0.816    | 1.40E+07 |
| 50 CR | 0.884    | 1.90E+08 |

72 hr

|       | final OD | CFU      |
|-------|----------|----------|
| 12230 | 0.837    | 2.20E+06 |
| 10 CR | 0.768    | 4.20E+06 |
| 50 CR | 0.814    | 2.45E+07 |

12A

12B

12C

14A

VH

14B

VL1

14C

VL2

FUSOBACTERIUM NUCLEATUM AMYLOID-LIKE FadA FOR DIAGNOSIS AND TREATMENT OF FN-MEDIATED PATHOGENESIS

CROSS-REFERENCE TO RELATED APPLICATIONS

This application is a continuation of PCT International Application No. PCT/US2022/023479, filed Apr. 5, 2022, claiming the benefit of U.S. Provisional Application No. 63/172,971, filed Apr. 9, 2021, the contents of each of which are hereby incorporated by reference into the subject application.

STATEMENT OF GOVERNMENTAL INTEREST

This invention was made with government support under grants CA192111, DE014924 and DE029532 awarded by the National Institutes of Health. The government has certain rights in the invention.

This application incorporates-by-reference nucleotide sequences which are present in the file named "1231115 91898 A PCT A Substitute Sequence Listing SI.xml", which is 44 kilobytes in size, and which was created on Nov. 14, 2023, in the IBM-PC machine format, having an operating system compatibility with MS-Windows, which is contained in the xml file filed Nov. 15, 2023 as part of this application.

BACKGROUND

*Fusobacterium nucleatum* (Fn) is a filamentous Gram-negative anaerobe ubiquitous in the oral cavity. As an opportunistic commensal, it is the most predominant core component in the subgingival microbiome in both health and disease. Outside the oral cavity, Fn is absent or infrequently detected under healthy conditions (Segata et al, 2012). Under disease conditions, however, Fn is one of the most prevalent species involved in organ abscesses, atherosclerosis, pregnancy complications, rheumatoid arthritis, respiratory tract infections, and GI disorders, e.g., appendicitis, inflammatory bowel disease, esophageal, gastric, pancreatic and colorectal cancers (CRC) (Castellarin et al, 2012; Han et al, 2010; Han et al, 2009; Hsieh et al, 2018; Kostic et al, 2012; Liu et al, 2019; Mitsuhashi et al, 2015; Ortiz et al, 2009; Strauss et al, 2011; Swidsinski et al, 2011; Thomas et al, 2019; Wang et al, 2013). It is not known how Fn acts both as a common commensal as well as a rampant pathogen. Understanding the underlying molecular signal and mechanism is critical for controlling Fn pathogenesis.

Several lines of evidence implicate that the FadA adhesin (for *Fusobacterium* adhesin A) plays a critical role in the pathogenicity of Fn. FadA is conserved among Fn, *Fusobacterium periodonticum* and *Fusobacterium necrophorum*, but absent in most other Fusobacteria (Han et al, 2005; Umana et al, 2019). In human colonic tissues, the fadA gene levels increase stepwise from normal to adenoma, and from adenoma to carcinoma (Rubinstein et al, 2013). Meta-analysis of diverse populations showed that fadA is also consistently enriched in the fecal microbiome of CRC patients (Wirbel et al, 2019). The pathogenesis mechanisms of FadA in CRC and pregnancy complications have been reported previously (Ikegami et al, 2009; Rubinstein et al, 2019; Rubinstein et al., 2013). FadA mediates Fn binding and invasion of epithelial and endothelial cells, and colonization in the placenta (Fardini et al, 2011; Han et al., 2005; Ikegami et al., 2009; Xu et al, 2007). It binds VE-cadherin on endothelial cells, loosening of the cell-cell junctions and enabling systemic bacterial dissemination (Fardini et al., 2011; Ikegami et al., 2009). FadA is required for Fn to colonize murine placenta (Ikegami et al., 2009). It also enables Fn to preferentially bind CRC cells expressing Annexin A1, a β-catenin modulator required for CRC cell growth. Upon binding to CRC cells, FadA further elevates Annexin A1 expression. This positive feedback loop between FadA and Annexin A1 exacerbates CRC progression (Rubinstein et al., 2019). While the implication of FadA in various pathologies is well documented, how this virulence factor functions in health and disease is not known. In this study, we report that FadA undergoes dramatic biochemical changes to become "amyloid-like" to enhance Fn virulence.

Amyloids are fibrous protein aggregates that are implicated in numerous human diseases such as Alzheimer's, Parkinson's, and prion diseases. A related, but biochemically distinct, group of protein aggregates is known as 'amyloid-like'. This class shares a subset of biochemical properties of the disease-related amyloids such as fiber formation, stable cross-beta sheets, and/or resistance to ionic detergents (Berchowitz et al, 2015; Boke et al, 2016). FadA readily forms fibers in vitro with a diameter similar to well-studied amyloids (Nithianantham et al, 2009). We investigated whether FadA can also form amyloid-like structures.

The present disclosure identifies the existence, and role, of Fn amyloid-like FadA in disease states and provides compositions, treatments and methods for treating conditions related to Fn amyloid-like FadA.

SUMMARY

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising:

a heavy chain comprising:

CDR1 having the sequence GYTFTTYW (SEQ ID NO:1);

CDR2 having the sequence INPNTDYT (SEQ ID NO:2);

CDR3 having the sequence ARSGYFGSRYYFDY (SEQ ID NO:3);

and either a light chain comprising:

CDR1 having the sequence QSLANSYGNTY (SEQ ID NO:4);

CDR2 having the sequence GIS (SEQ ID NO:5);

CDR3 having the sequence LQGTHQPPT (SEQ ID NO:6);

or a light chain comprising:

CDR1 having the sequence QDINKY (SEQ ID NO:7);

CDR2 having the sequence YTS (SEQ ID NO:8);

CDR3 having the sequence LQYDYLLH (SEQ ID NO:9).

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising:

a heavy chain comprising:

CDR1 having the sequence GYTFTTYW (SEQ ID NO:1);

CDR2 having the sequence INPNTDYT (SEQ ID NO:2);
CDR3 having the sequence ARSGYFGSRYYFDY (SEQ ID NO:3);
and
a light chain comprising:
CDR1 having the sequence QSLANSYGNTY (SEQ ID NO:4);
CDR2 having the sequence GIS (SEQ ID NO:5);
CDR3 having the sequence LQGTHQPPT (SEQ ID NO:6.

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising:
a heavy chain comprising:
CDR1 having the sequence GYTFTTYW (SEQ ID NO:1);
CDR2 having the sequence INPNTDYT (SEQ ID NO:2);
CDR3 having the sequence ARSGYFGSRYYFDY (SEQ ID NO:3);
and
a light chain comprising:
CDR1 having the sequence QDINKY (SEQ ID NO:7);
CDR2 having the sequence YTS (SEQ ID NO:8);
CDR3 having the sequence LQYDYLLH (SEQ ID NO:9).

A pharmaceutical composition comprising an antibody which binds Fn amyloid-like FadA, or a Fn amyloid-like FadA-binding fragment thereof, or a Fn amyloid-like FadA-binding fusion protein as described herein, and a carrier.

A method of preventing or treating disease in a subject in a subject in need thereof comprising administering to the subject a therapeutically effective amount of an agent which inhibits or blocks an amyloid-like FadA secreted from *Fusobacterium nucleatum* (Fn).

A method of reducing development of or treating disease associated with Fn amyloid-like FadA in a subject, comprising administering to the subject an amount of an agent which inhibits, blocks or binds a *Fusobacterium nucleatum* amyloid-like adhesin A FadA (Fn amyloid-like FadA) effective to reduce development of or treat a disease associated with Fn amyloid-like FadA.

A therapeutic mouthrinse comprising i) an amount of an agent which inhibits, blocks or binds a *Fusobacterium nucleatum* amyloid-like adhesin A (Fn amyloid-like FadA) and ii) a liquid carrier.

A method of treating an oral or dental disease in a subject associated with pathogenic, oral *Fusobacterium nucleatum* (Fn) comprising administering an amount of the therapeutic mouthrinse as described herein effective to treat the oral or dental disease.

A method of inhibiting *Fusobacterium nucleatum* (Fn)-mediated stimulation of a colon cancer in a subject comprising administering an amount of an antibody, or Fn amyloid-like FadA-binding fragment, or Fn amyloid-like FadA-binding fusion protein as described herein or pharmaceutical composition comprising such, or an amount of Bapineuzumab, Solanezumab, Gantenerumab, Crenezumab, Ponezumab, Aducanumab, or BAN2401, effective to inhibit Fn-mediated stimulation of a colon cancer.

A method of diagnosing a disease in a tissue or organ of a subject as being associated with pathogenic *Fusobacterium nucleatum* comprising quantifying the amount of *Fusobacterium nucleatum* amyloid-like adhesin A (Fn amyloid-like FadA) in a sample of the tissue or organ and comparing the level of the Fn amyloid-like FadA in the sample to a reference value of the expression level of Fn amyloid-like FadA, wherein a level Fn amyloid-like FadA in the sample above the reference value indicates that the disease is associated with pathogenic *Fusobacterium nucleatum*.

A method of detecting a disease in a subject comprising:
assaying a sample from the subject for the expression level of *Fusobacterium nucleatum* amyloid-like adhesin A (Fn amyloid-like FadA);
comparing the level of the Fn amyloid-like FadA in the sample to a known reference value of the expression level of Fn amyloid-like FadA;
detecting that the subject has a disease if the level of the expression of Fn amyloid-like FadA is increased as compared to the reference value.

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, for use as a medicament in treating a cancer or a dental disease.

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising complementary-determining regions CDR1 through CDR6, wherein one or more of CDR1 through CDR6 has 85% or greater identity with, but not 100% identity with, the CDR1 through CDR6 sequences set forth as follows:
a heavy chain comprising:
CDR1 having the sequence GYTFTTYW (SEQ ID NO: 1);
CDR2 having the sequence INPNTDYT (SEQ ID NO:2);
CDR3 having the sequence ARSGYFGSRYYFDY (SEQ ID NO:3);
and either
a light chain comprising:
CDR4 having the sequence QSLANSYGNTY (SEQ ID NO:4);
CDR5 having the sequence GIS (SEQ ID NO:5);
CDR6 having the sequence LQGTHQPPT (SEQ ID NO:6);
or
a light chain comprising:
CDR4 having the sequence QDINKY (SEQ ID NO:7);
CDR5 having the sequence YTS (SEQ ID NO:8);
CDR6 having the sequence LQYDYLLH (SEQ ID NO:9).

A nucleic acid encoding a heavy chain of an antibody described herein.

A nucleic acid encoding a light chain of an antibody described herein.

A hybridoma comprising a nucleic acid as described herein.

BRIEF DESCRIPTION OF THE DRAWINGS

FIG. 2A-2G. Pre-FadA as a key component of amyloid-like FadA. 2A. Single-letter amino acid (aa) sequence of FadA (SEQ ID NO:28). The intact pre-FadA consists of 129 aa, with the first 18-aa (top row) constitute the signal peptide. The remaining 111 aa constitute mFadA. The residues that are replaced in the mutant proteins used in this study are shown in red. 2B. Analysis of detergent resistant recombinant FadA polymers expressed in E. coli. An aliquot of 50 µg detergent-resistant pellets prepared from E. coli BL21(DE3) carrying the cloning vector pET21(b), pYWH417-6 (p_FadAc), or pYWH418 (p_mFadA) were analyzed by SDD-AGE, followed by Western blot analysis. FadA polymers were only detected in E. coli expressing FadAc, but not in mFadA or the vector control. 2C. Reactivity of recombinant FadA and its variants with anti-amyloid fibril antibody OC. A total of 10 µg each of recombinant protein mFadA, FadAc, FadA-L-9A, FadA-L14A, FadA-S71A, and FadA-L76A purified from E. coli was slot-blotted onto nitrocellulose and incubated with polyclonal OC antibody at 1:5,000 dilution. Amyloid-like recombinant Rim4 (Berchowitz et al., 2015) was used as a positive control and histone H1 was used as a negative control. Ponceau stain (pink color) is shown as a loading control. 2D. Thioflavin-T binding assay. FadA proteins at indicated concentrations were incubated with 10 µM Thioflavin-T at room temperature for 10 min. The fluorescent intensity was measured at excitation wavelength of 440 nm and emission wavelength of 500 nm. The experiment was performed in duplicate and repeated three times. *$p<0.05$, $p<0.01$, *$p<0.001$ (compared to BSA, t-test). 2E. Thioflavin-T binding assay in the presence of 0.1% SDS. FadA proteins (0.8 mg/ml) were incubated with 10 µM Thioflavin-T at room temperature for 10 min. The fluorescent intensity was measured at excitation wavelength of 440 nm and emission wavelength of 500 nm. The experiment was performed in duplicate and repeated three times. *$p<0.05$, **$p<0.01$ (compared to BSA, t-test). 2F. Western blot analysis of Fn12230 (Fn), fadA-deletion mutant US1 (ΔfadA) and spontaneous mutant lam following SDS-PAGE. A total of 400 µl of each culture grown to OD600 of 1.0 was pelleted and loaded onto 12% SDS-PAGE. FadA protein was detected using anti-FadA mAb 7H7 at 1:4,000 dilution. Compared to the wild type, lam produced significantly less pre-FadA, but not mFadA. 2G. Analysis of amyloid-like FadA produced by Fn 23726 and its Δfap2 mutant. An aliquot of 50 µg detergent-resistant pellets was loaded onto each lane, followed by SDD-AGE and Western blot analysis as described above. The mutant produced significantly less amyloid-like polymers than the wild type.

FIG. 5A-5D. Amyloid-like FadA mediates colonization in CRC and promotes tumor growth in vivo. 5A. Analysis of Fn colonization in mouse xenograft tumors by IHC. An inoculum of 5×106 HCT116 cells was injected subcutaneously and bilaterally into the nude mice. Once the tumors became visible (after 3-4 days), approximately 5×10⁶ CFU of Fn 12230 washed in PBS or 1 mg/ml Congo Red (CR) were injected into the tumors. The tumors were extracted one week later, and the formalin-fixed and embedded (FFPE) tissues were stained with mAb 7H7. Note the brown stains in tumor injected with PBS-washed tumor, but not in CR-washed tumor. 5B. Effects of secreted amyloid-like FadA on tumor growth. HCT116 cells were injected into the nude mice as described above, followed by injection of 5×106 CFU of Fn 12230 (Fn, n=7), lam (n=3) or US1 (ΔfadA, n=4). The tumor volumes were measured immediately before bacteria injection (Day 0, designated as 100%), and at 3 days after injection (Day 3). The horizontal lines represent averages of tumor volumes (left panel). The individual tumors are shown (right panel). $p<0.01$, *$p<0.001$ (t-test). 5C. Effect of anti-amyloid antibody OC on FadAc-mediated tumor growth. HCT116 cells were injected into the nude mice (n=6) as described above, followed by injection of 4 μl of 2 mg/ml FadAc mixed with 6 μl OC antibody or rabbit IgG control (rIgG) into tumors on the opposite sides. The tumor volumes were measured on Day 0 and Day 5 as described above. The horizontal lines represent the averages (left panel). The individual tumor pairs are shown (right panel, n=6). *$p<0.05$, **$p<0.01$ (t-test). 5D. Effect of detergent-resistant pellets prepared from Fn 12230 (Fn) and US1 (ΔfadA) on tumor growth. HCT116 cells were inoculated into the nude mice as described above. In one group of mice (n=3), sarkosyl-resistant pellets prepared from Fn 12230 and US1 (ΔfadA) were injected into the tumors on opposite sides. In another group (n=6), sarkosyl-resistant pellets prepared from Fn 12230 were mixed with OC or rabbit IgG control (rIgG) before injecting into the tumors on opposite sides. The tumor volumes were measured described above. The vertical lines represent the standard deviations. The individual tumor pairs are shown (right panel). *$p<0.05$, $p<0.01$, *$p<0.001$ [compared to US1 (ΔfadA), t-test].

Figure 6A:
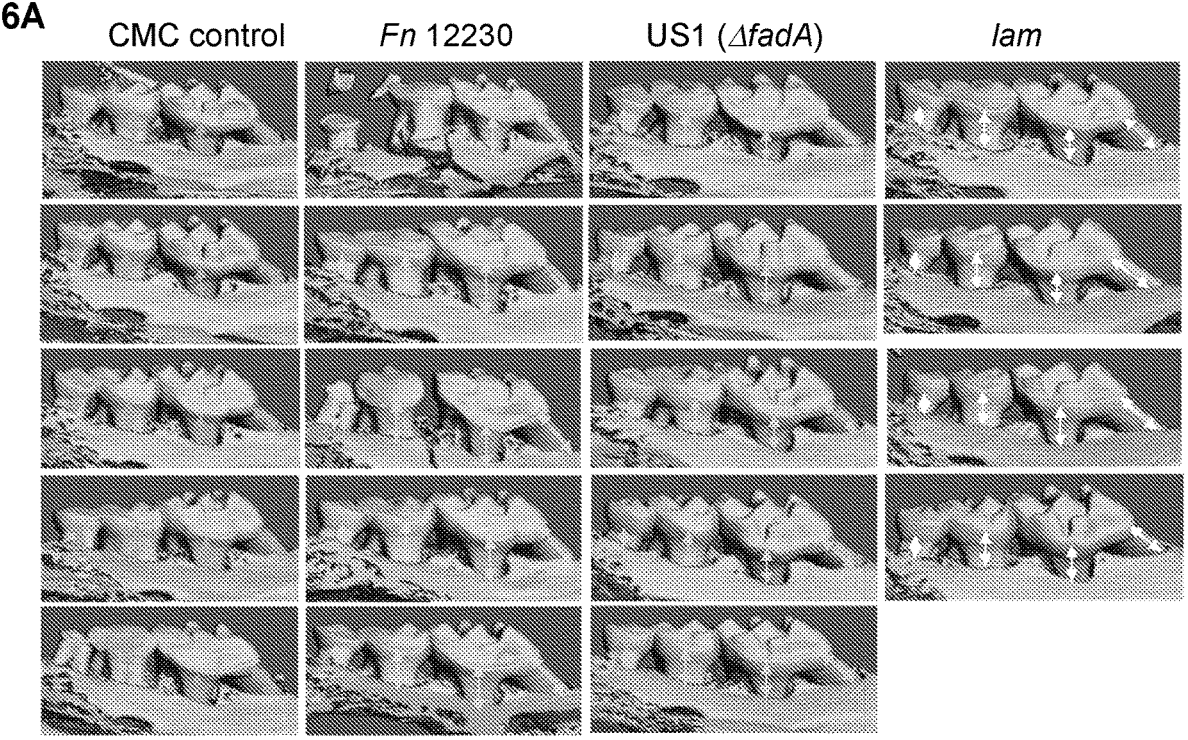
Figure 6B:
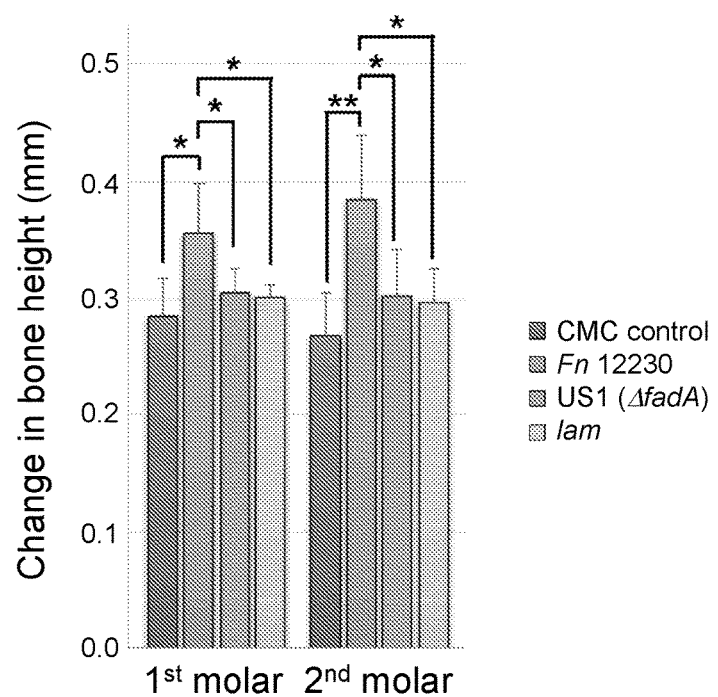

FIG. 6A-6B. Amyloid-like FadA induces periodontal bone loss in mice. 6A. Approximately 1×10⁹ CFU of Fn 12230, US1 (ΔfadA), and lam suspended in carboxymethylcellulose (CMC) were orally administered to C57BL/6 mice three times a week for 10 weeks. CMC alone was administered as a control. Maxillae from mice inoculated with CMC alone (n=5), Fn 12230 (n=5), US1 (ΔfadA; n=5), and lam (n=4) were harvested and fixed in 4% paraformaldehyde and stored in 70% ethanol, followed by micro CT (μCT) scanning using a Scanco vivaCT 80 system at 55 kVp, 145 μA, and 250 ms integration time. Shown in the Fig. are reconstructed grayscale images. ImageJ was used to measure difference in bone height from the cementoenamel junction (CEJ) to the alveolar crest between palatal roots of first and second molars (see arrows). 6B. The average bone loss of each group shown in A, with the lines above each bar representing standard deviations. *$p<0.05$. **$p<0.01$ (t-test).

Figure 7:
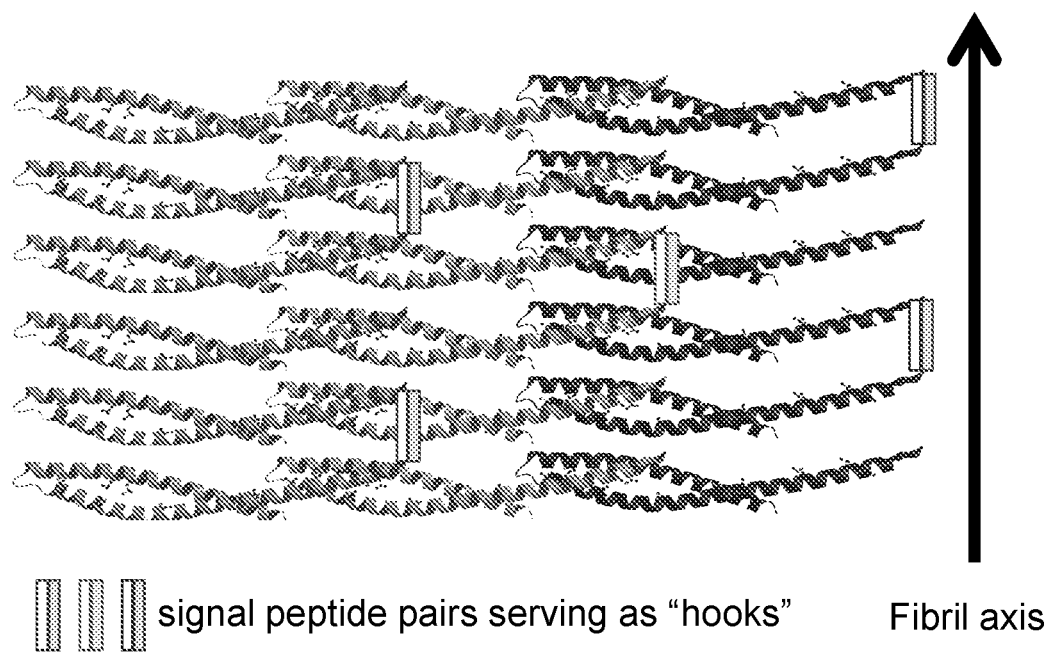

FIG. 7. A proposed model of the structure of amyloid-like FadA. The FadA filaments were based on the crystal structure of mFadA (Nithianantham et al., 2009), with the addition of intercalating pre-FadA. The signal peptide pairs from two neighboring filaments (one clear bar and one shaded bar) bind to each other through hydrophobic interactions, serving as "hooks" crosslinking the filaments so that the filaments are stacked perpendicular to the fibril axis into fibrous sheets.

Figure 8A:
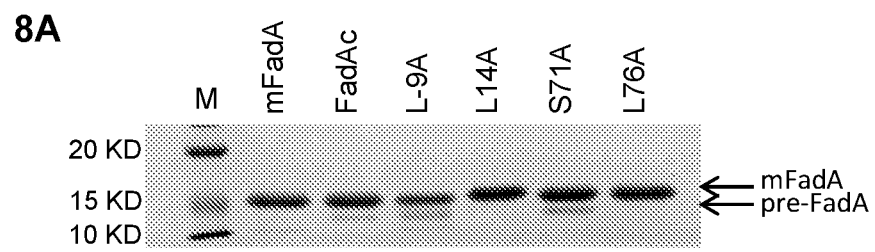
Figure 8B:
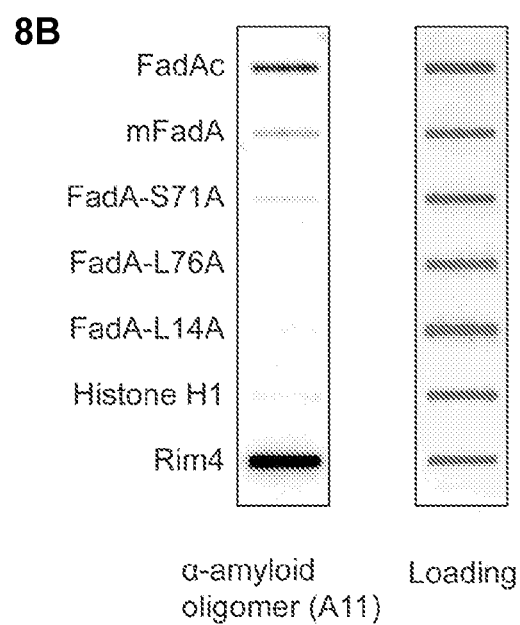
Figure 8C:
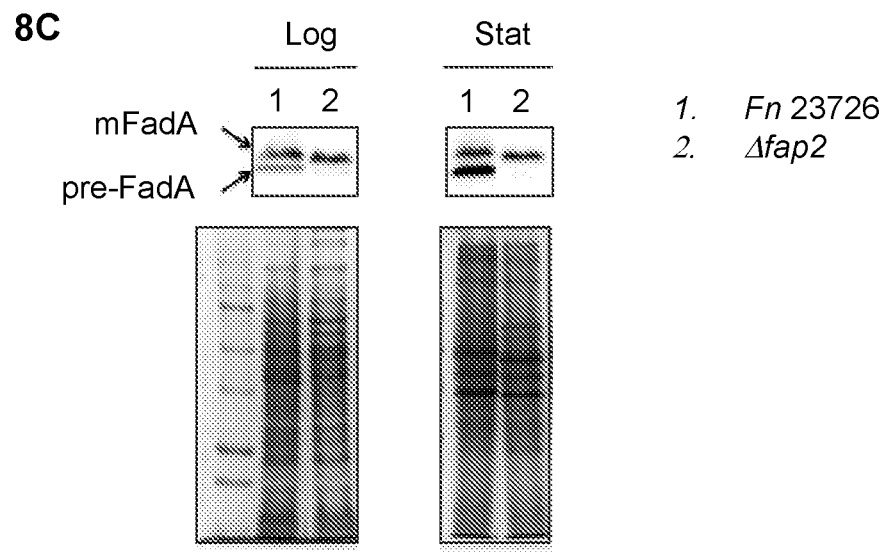

FIG. 8A-8C. 8A. SDS-PAGE analysis of recombinant FadAc and its variants. The proteins were purified as previously described (Xu et al., 2007). Approximately 2.5 μg of each purified protein were loaded onto 12% SDS-PAGE. Following electrophoresis, the gel was stained with Coomassie Blue G-250. 8B. Reactivities of recombinant FadA and its variants with anti-amyloid oligomer antibody A11. A total of 10 μg each of recombinant protein mFadA, FadAc, FadA-L-9A, FadA-L14A, FadA-S71A, and FadA-L76A purified from *E. coli* was slot-blotted onto nitrocellulose and incubated with polyclonal anti-amyloid oligomer antibody A11 at 1:5,000 dilution. Amyloid-like recombinant Rim4 (Berchowitz et al., 2015) was used as a positive control and histone H1 was used as a negative control. Ponceau stain (pink color) is shown as a loading control. 8C. Western blot analysis of wild-type Fn 23726 (1) and mutants Δfap2 (2) using anti-FadA mAb 7H7. The bottom panel is Coomassie blue stain for loading control.

Figure 9:
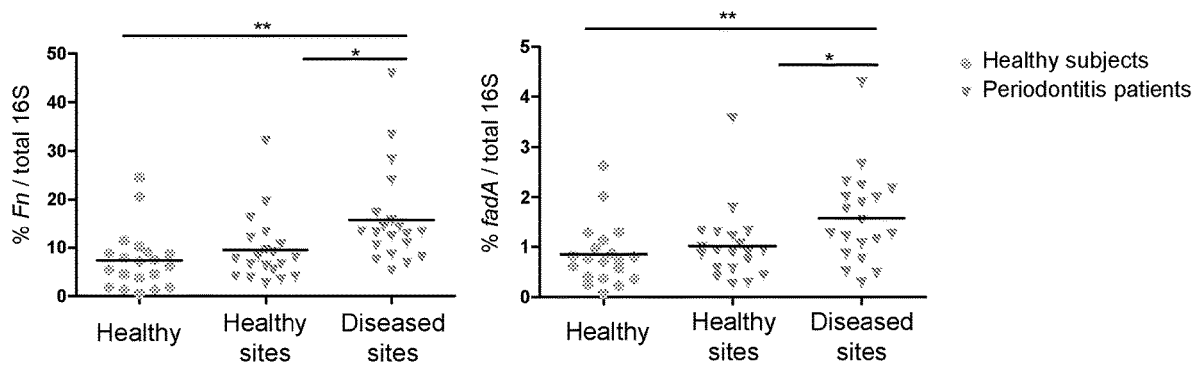

FIG. 9. Quantification of Fn and fadA gene copies in subgingival plaque samples. DNA was extracted from subgingival bacterial plaque samples from two groups of participants: periodontal healthy subjects (n=20) and patients with periodontitis (n=20). For the latter group, subgingival plaques were collected from healthy sites (probing depth ≤3 mm) as well as diseased sites (probing depth ≥7 mm). Gene copy numbers of total 16S rRNA, Fn 16S rRNA, and fadA genes were measured using DNA and determined using the standard curves. The percentages of Fn 16S rRNA (left panel) and fadA gene (right panel) levels relative to total 16S RNA gene levels of each patient were calculated. The horizontal bars represent the mean values. *p<0.05, **p<0.01 (One-way ANOVA).

Figures 10A, 10B:
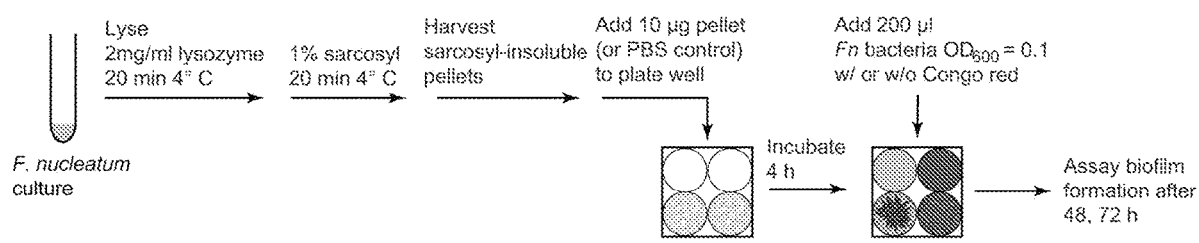

FIG. 10A-10B. 10A. Schematic illustration of preparation of detergent-resistant bacterial pellets and its use as scaffold for biofilm growth. 10B. Effects of Congo Red on Fn viability. Fn 12230 was incubated in PBS (top row), 10 mg/ml Congo Red (10 CR), or 50 mg/ml Congo Red (50 CR) for 48 hrs (left panel) or 72 hrs (right panel), followed by measurement of OD600 (OD) and viable counts (CFU).

Figure 11A:
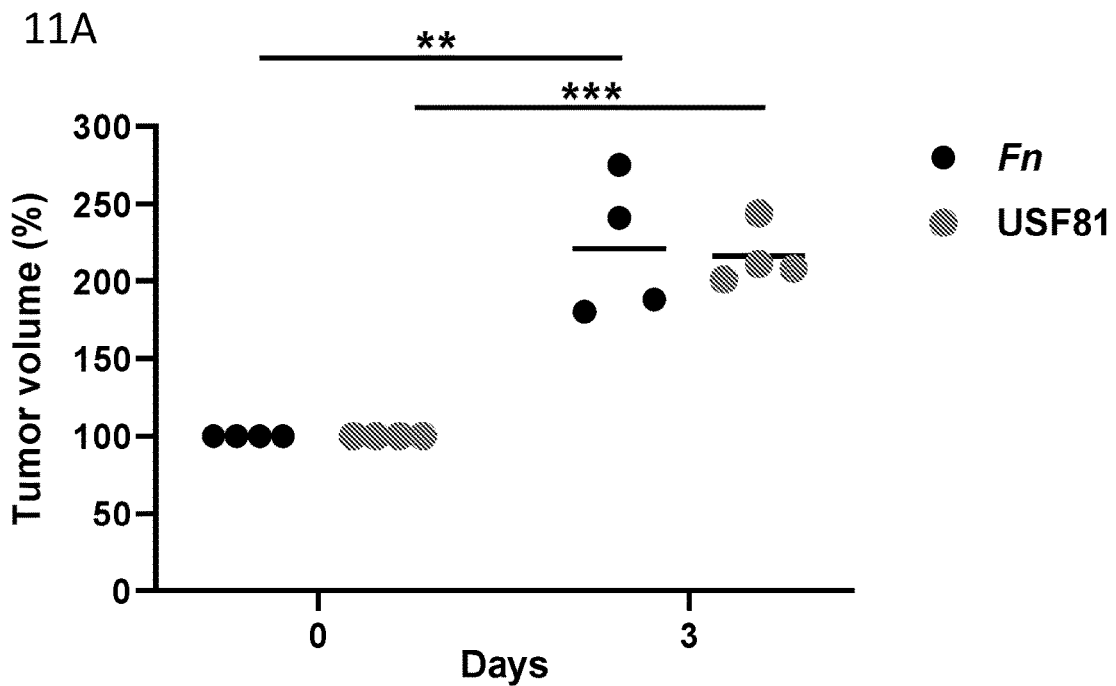
Figure 11B:
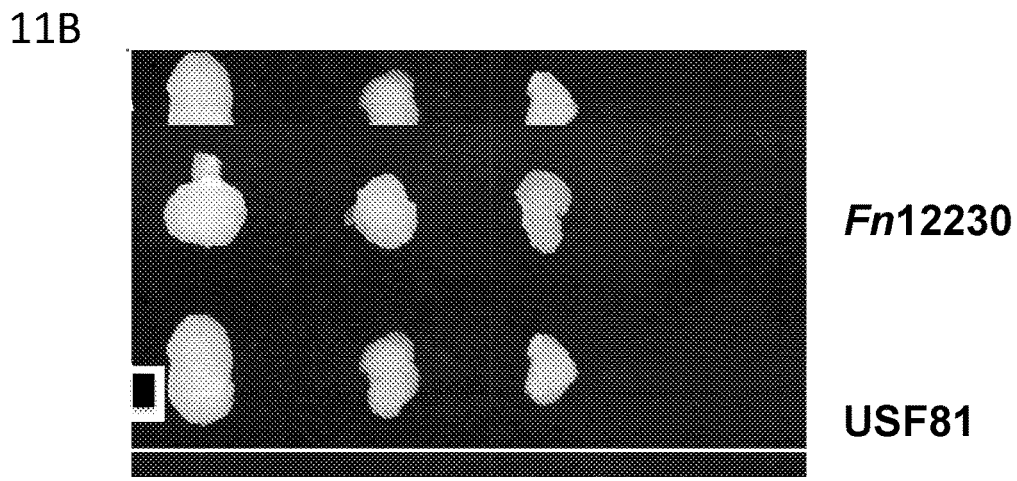

FIG. 11A-11B. The fadA-complementing strain restores CRC growth stimulation. 11A. HCT116 cells were inoculated subcutaneously and bilaterally into the nude mice (n=4), followed by injection of $5 \times 10^6$ CFU of Fn 12230 and the fadA-complementing clone USF81 on opposite sides as described. The tumor volumes were measured on Day 0 and 3 as described. The horizontal lines represent averages of tumor volumes (top panel). 11B. The individual tumors are shown (bottom panel). p<0.01, *p<0.001 (t-test).

Figure 12A:
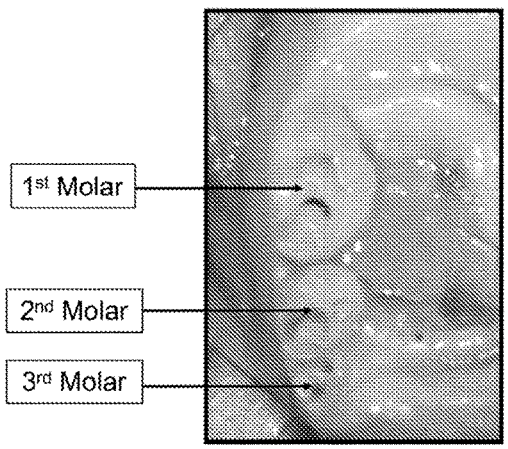
Figure 12B:
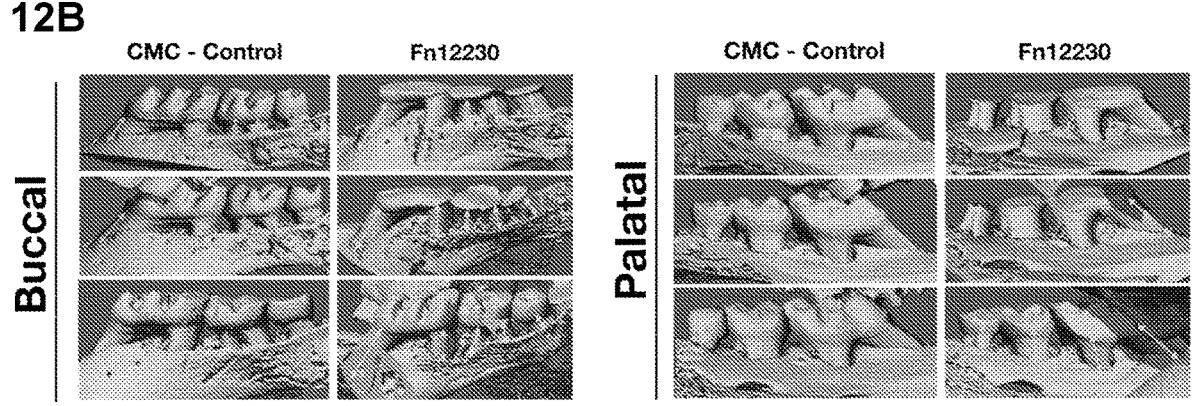
Figure 12C:
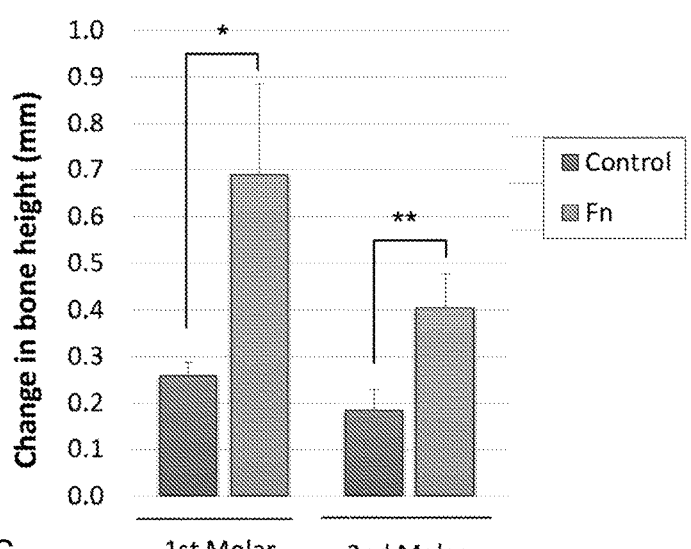

FIG. 12A-12C. Fn 12230 induces periodontal bone loss in mice. 12A. Image showing first, second and third molars in the upper jaw of a mouse. 12B. Approximately $1 \times 10^9$ CFU of Fn 12230 suspended in carboxymethylcellulose were orally administered to C57BL/6 mice four times a week for 10 weeks. CMC alone was administered as a control. Maxillae from mice inoculated with CMC alone (n=3) and Fn 12230 (n=3) were harvested and fixed in 4% paraformaldehyde and stored in 70% ethanol, followed by μCT scanning using a Scanco vivaCT 80 system at 55 kVp, 145 μA, and 250 ms integration time. Shown in the Fig. are reconstructed grayscale images. ImageJ was used to measure difference in bone height from the cementoenamel junction (CEJ) to the alveolar crest of first and second molars (see arrows). 12C. The average bone loss of each group is shown by the colored bars, with the lines above each bar representing standard deviations. *p<0.05. **p<0.01 (t-test).

Figure 13:
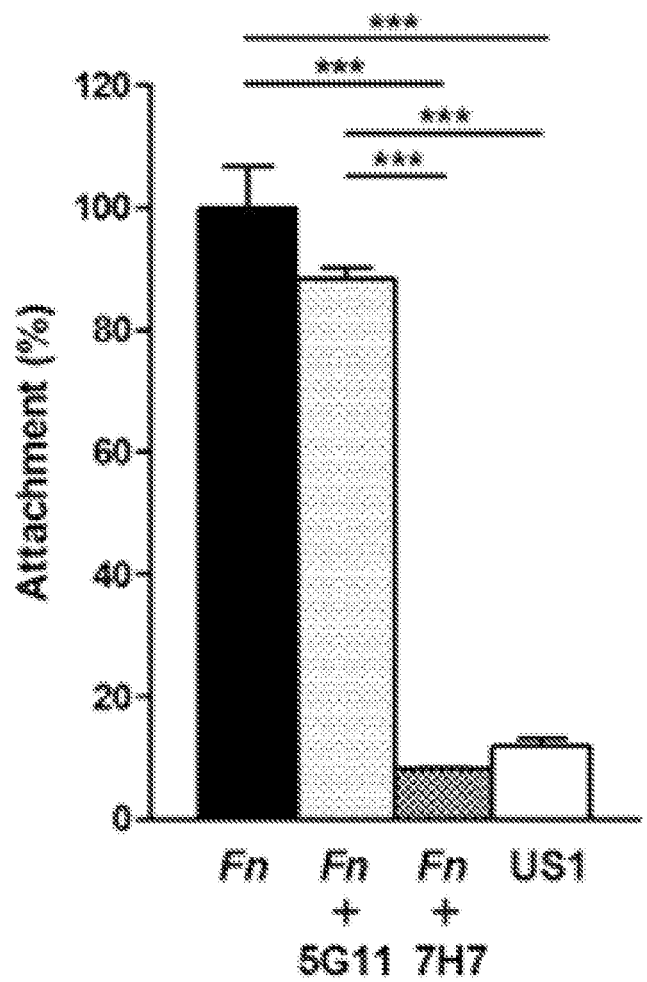

FIG. 13: Inhibition of Fn binding to HCT116 by mAb 7H7: Method: Fn 12230 (Fn) was mixed with 20 μl anti-FadA mAb 5G11, or 7 anti-FadA mAb 7H7, before adding to the monolayers at multiplicity of infection (MOI) of 50:1. US1 (ΔfadA) was included as a negative control. The attachment level by Fn alone was designated as 100%, to which all other values were expressed in comparison. Data shown are mean values±SEM. The experiment was performed in duplicate and repeated four times. ***p<0.001.

Figure 14A:
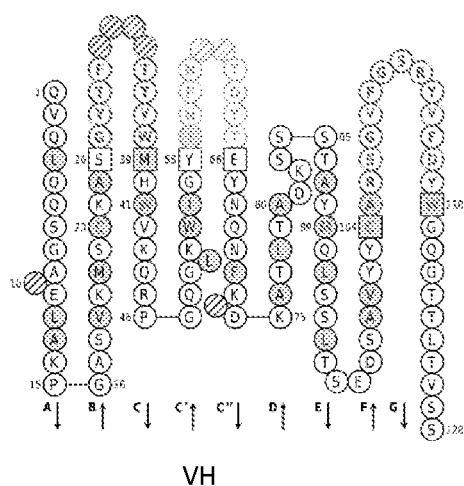
Figure 14B:
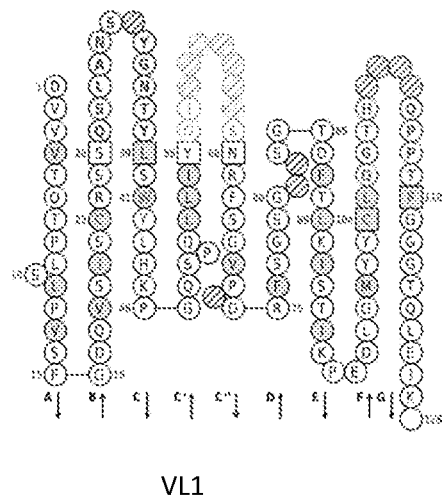
Figure 14C:
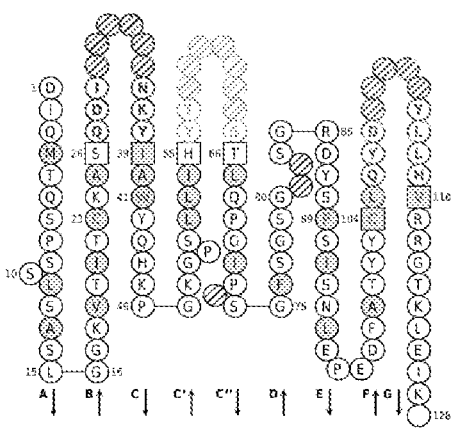

FIG. 14A-14C: Antibody against Fn amyloid-like FadA. 14A VH sequence of anti-Fn amyloid-like FadA antibody. 14B: VL sequence #1. 14C: VL sequence #2.

DETAILED DESCRIPTION

An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising:

a heavy chain comprising:
CDR1 having the sequence GYTFTTYW (SEQ ID NO: 1);
CDR2 having the sequence INPNTDYT (SEQ ID NO:2);
CDR3 having the sequence ARSGYFGSRYYFDY (SEQ ID NO:3);
and either
a light chain comprising:
CDR1 having the sequence QSLANSYGNTY (SEQ ID NO:4);
CDR2 having the sequence GIS (SEQ ID NO:5);
CDR3 having the sequence LQGTHQPPT (SEQ ID NO:6);
or
a light chain comprising:
CDR1 having the sequence QDINKY (SEQ ID NO:7);
CDR2 having the sequence YTS (SEQ ID NO:8);
CDR3 having the sequence LQYDYLLH (SEQ ID NO:9).

In an embodiment, the antibody, Fn amyloid-like FadA-binding fragment thereof, or Fn amyloid-like FadA-binding fusion protein light chain comprises:
CDR1 having the sequence QSLANSYGNTY (SEQ ID NO:4);
CDR2 having the sequence GIS (SEQ ID NO:5); and
CDR3 having the sequence LQGTHQPPT (SEQ ID NO:6.

In an embodiment, the antibody, Fn amyloid-like FadA-binding fragment thereof, or Fn amyloid-like FadA-binding fusion protein light chain comprises:
CDR1 having the sequence QDINKY (SEQ ID NO:7);
CDR2 having the sequence YTS (SEQ ID NO:8); and
CDR3 having the sequence LQYDYLLH (SEQ ID NO:9).

In embodiments, the antibody, Fn amyloid-like FadA-binding fragment, or Fn amyloid-like FadA-binding fusion protein comprise framework regions of a light chain and/or a heavy chain which are human framework regions or have 85% or more sequence identity therewith.

In embodiments, the antibody is a humanized antibody.

In embodiments, the antibody or antigen-binding fragment thereof has a human sequence Fc region or has 85% or more sequence identity therewith.

In embodiments, the antibody or fragment thereof is chimeric.

In embodiments, the antibody is a monospecific antibody comprising two heavy chains of identical sequence and two light chains of identical sequence.

In embodiments, the antibody is a monoclonal antibody.

In embodiments, the antibody is an IgG1(λ) or an IgG4 (λ). In embodiments, the antibody is an IgG2(λ).

In embodiments, the Fn amyloid-like FadA-binding fragment is an Fab fragment, an Fab' fragment, or an F(ab)' fragment.

In embodiments, the Fn amyloid-like FadA-binding fragment is a single chain variable fragment (scFv).

A pharmaceutical composition is provided comprising an antibody which binds Fn amyloid-like FadA, or a Fn amyloid-like FadA-binding fragment thereof, or a Fn amyloid-like FadA-binding fusion protein, as described herein, and a carrier.

A method is provided of preventing or treating disease in a subject in a subject in need thereof comprising administering to the subject a therapeutically effective amount of an agent which inhibits or blocks an amyloid-like FadA secreted from *Fusobacterium nucleatum* (Fn).

A method is provided of reducing development of or treating disease associated with Fn amyloid-like FadA in a subject, comprising administering to the subject an amount of an agent which inhibits, blocks or binds a *Fusobacterium nucleatum* amyloid-like adhesin A FadA (Fn amyloid-like FadA) effective to reduce development of or treat a disease associated with Fn amyloid-like FadA.

In embodiments, the agent is an antibody, or Fn amyloid-like FadA-binding fragment, or Fn amyloid-like FadA-binding fusion protein as described herein.

In embodiments, the agent is Bapineuzumab, Solanezumab, Gantenerumab, Crenezumab, Ponezumab, Aducanumab, or BAN2401.

In embodiments, the agent is an antibody, and is a monoclonal antibody.

In embodiments, the agent is the pharmaceutical composition described herein.

In embodiments, the disease is associated with extra-oral *Fusobacterium nucleatum* in the subject.

In embodiments, the disease is a cancer, atherosclerosis, rheumatoid arthritis, a respiratory tract infection, or a gastrointestinal disorder.

In embodiments, the disease is a cancer. In embodiments, the cancer is pancreatic or colorectal.

In embodiments, the disease is associated with pathogenic, oral *Fusobacterium nucleatum* in the subject.

In embodiments, the disease is a dental disease.

In embodiments, the dental disease is periodontal bone loss.

In embodiments, the methods further comprise administering an anti-anaerobic bacteria antibiotic to the subject.

In embodiments, the agent is administered systemically or locally.

In embodiments, the antibiotic is administered systemically or locally.

In embodiments, the disease is colorectal cancer and the agent and/or antibiotic is administered rectally.

In embodiments, the antibiotic is a nitroimidazole.

In embodiments, the nitroimidazole is metronidazole.

A therapeutic mouthrinse is provided comprising i) an amount of an agent which inhibits, blocks or binds a *Fusobacterium nucleatum* amyloid-like adhesin A (Fn amyloid-like FadA) and ii) a liquid carrier.

In embodiments, the agent is an antibody, or Fn amyloid-like FadA-binding fragment, or Fn amyloid-like FadA-binding fusion protein, of any of Claims 1-14, Bapineuzumab, Solanezumab, Gantenerumab, Crenezumab, Ponezumab, Aducanumab, or BAN2401.

A method is provided of treating an oral or dental disease in a subject associated with pathogenic, oral *Fusobacterium nucleatum* (Fn) comprising administering an amount of the therapeutic mouthrinse of as described herein effective to treat the oral or dental disease.

In embodiments, the oral or dental disease is periodontal bone loss.

A method of inhibiting *Fusobacterium nucleatum* (Fn) mediated stimulation of a colon cancer in a subject comprising administering an amount of an antibody, or Fn amyloid-like FadA-binding fragment, or Fn amyloid-like FadA-binding fusion protein as described herein or pharmaceutical composition comprising such, or an amount of Bapineuzumab, Solanezumab, Gantenerumab, Crenezumab, Ponezumab, Aducanumab, or BAN2401, effective to inhibit Fn-mediated stimulation of a colon cancer.

In embodiments, the subject does not have, or has not been diagnosed with, a dementia.

In embodiments, the subject does not have, or has not been diagnosed with, Alzheimer's disease.

In embodiments, the methods further comprise obtaining, or having obtained, an identification of the subject as having Fn amyloid-like FadA pathogenic *Fusobacterium nucleatum* (Fn) resident in their body.

In embodiments, the presence of *Fusobacterium nucleatum* (Fn) is determined from detecting or quantifying an amount of Fn amyloid-like FadA in a sample from the subject and comparing the level of the Fn amyloid-like FadA in the sample to a reference value of the expression level of Fn amyloid-like FadA, wherein an amount in excess of the reference value indicates that the subject has a level of pathogenic Fn.

In embodiments, detecting or quantifying an amount of Fn amyloid-like FadA in a sample comprises contacting the sample, or a derivative from the sample, with an agent that binds Fn amyloid-like FadA.

In embodiments, the agent is an antibody or antibody fragment as described herein, or is an antibody that binds Fn amyloid-like FadA.

In embodiments, two or more different antibodies or antibody fragments are used to contact the sample or derivative from the sample.

In embodiments, the agent is Congo Red or Thioflavin-T.

In embodiments, the agent is conjugated to a detectable marker.

Fn amyloid-like FadA complexes are generated from Fn, and they do not encompass human amyloid proteins as generated from human cells.

A method is provided of diagnosing a disease in a tissue or organ of a subject as being associated with pathogenic *Fusobacterium nucleatum* comprising quantifying the amount of *Fusobacterium nucleatum* amyloid-like adhesin A (Fn amyloid-like FadA) in a sample of the diseased tissue or organ and comparing the level of the Fn amyloid-like FadA in the sample to a reference value of the expression level of Fn amyloid-like FadA, wherein a level Fn amyloid-like FadA in the sample above the reference value indicates that the disease is associated with pathogenic *Fusobacterium nucleatum*.

A method is provided of detecting a disease in a subject comprising:
  assaying a sample from the subject for the expression level of *Fusobacterium nucleatum* amyloid-like adhesin A (Fn amyloid-like FadA);
  comparing the level of the Fn amyloid-like FadA in the sample to a known reference value of the expression level of Fn amyloid-like FadA;
  detecting that the subject has a disease if the level of the expression of Fn amyloid-like FadA is increased as compared to the reference value.

In embodiments, the disease is a disease associated with Fn amyloid-like FadA.

In embodiments, the disease is a cancer, dental disease, atherosclerosis, rheumatoid arthritis, a respiratory tract infection, or a gastrointestinal disorder.

In embodiments, the disease is a cancer and is pancreatic or colorectal.

An antibody is provided which binds *Fusobacterium nucleatum* amyloid-like adhesin A (Fn amyloid-like FadA), or an Fn amyloid-like FadA-binding fragment thereof, or a Fn amyloid-like FadA-binding fusion protein as described herein for use as a medicament in treating a cancer or a dental disease.

In embodiments, the cancer is a colon cancer or a pancreatic cancer.

In embodiments, the dental disease is periodontal bone loss.

In embodiments, the antibody is Bapineuzumab, Solanezumab, Gantenerumab, Crenezumab, Ponezumab, Aducanumab, or BAN2401.

An antibody is provided which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising, comprising complementary-determining regions CDR1 through CDR6, wherein one or more of CDR1 through CDR6 has 85% or greater identity with, but not 100% identity with, the CDR1 through CDR6 sequences set forth as follows:

a heavy chain comprising:
CDR1 having the sequence GYTFTTYW (SEQ ID NO: 1);
CDR2 having the sequence INPNTDYT (SEQ ID NO:2);
CDR3 having the sequence ARSGYFGSRYYFDY (SEQ ID NO:3);
and either
a light chain comprising:
CDR4 having the sequence QSLANSYGNTY (SEQ ID NO:4);
CDR5 having the sequence GIS (SEQ ID NO:5);
CDR6 having the sequence LQGTHQPPT (SEQ ID NO:6);
or
a light chain comprising:
CDR4 having the sequence QDINKY (SEQ ID NO:7);
CDR5 having the sequence YTS (SEQ ID NO:8);
CDR6 having the sequence LQYDYLLH (SEQ ID NO:9).

A nucleic acid encoding a heavy chain of an antibody as described herein.

A nucleic acid encoding a light chain of an antibody as described herein.

In embodiments, the nucleic acid is an expression vector.

A hybridoma is provided comprising a nucleic acid as described herein.

In embodiments, the anti-Fn amyloid-like FadA antibody or fragment thereof of the invention, comprises (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02. In embodiments, the anti-Fn amyloid-like FadA or fragment thereof, comprises an optimized version of, having less than 100% sequence identity with, a (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02.

Fragments of antibodies can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In embodiments, a linker of the scFv is 10-25 amino acids in length. In an embodiment the peptide linker comprises glycine, serine and/or threonine residues. (For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain can be in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety).

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In contrast to polyclonal antibody preparations, which typically include different antibodies directed against different determinants (epitopes), each monoclonal antibody of a monospecific monoclonal antibody preparation is directed against a single determinant on an antigen. A bispecific antibody, recognizing two antigens, in one embodiment, can be manufactured from two monoclonal antibodies. In addition to their specificity, monoclonal antibody preparations are advantageous in that they are typically uncontaminated by other immunoglobulins. Thus, an identified monoclonal antibody can be produced by non-hybridoma techniques, e.g., by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature absent the hand of man.

In an embodiment the antibody is humanized. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDR1-3 of both the heavy and light chain of the antibodies described herein. In a preferred embodiment, framework (FR) residues of the murine mAb are replaced with corresponding human immunoglobulin variable domain framework (FR) residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin, and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are well known. Some are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Res. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more, or all, CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

The term "$K_d$", as used herein, is intended to refer to the dissociation constant of an antibody-antigen interaction. One way of determining the $K_d$ or binding affinity of antibodies to the Fn amyloid-like FadA can be by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiimide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110, the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used. For example, ELISA.

In embodiments, the antibody or antigen-binding fragment thereof or fusion protein binds to an Fn amyloid-like FadA with an affinity of 100.0 nM KD or stronger.

In embodiments, the antibody or antigen-binding fragment thereof or fusion protein binds to an Fn amyloid-like FadA with an affinity of 10.0 nM $K_D$ or stronger.

In embodiments, the antibody or antigen-binding fragment thereof or fusion protein binds to an Fn amyloid-like FadA with an affinity of 2.0 nM $K_D$ or stronger.

In embodiments, the antibody or antigen-binding fragment thereof or fusion protein binds to an Fn amyloid-like FadA with an affinity of 1.0 nM $K_D$ or stronger.

In embodiments, the antibody or antigen-binding fragment thereof or fusion protein binds to an Fn amyloid-like FadA with an affinity of 0.1 nM $K_D$ or stronger.

In embodiments, the antibodies of the invention have an $EC_{50}$ for the antigen Fn amyloid-like FadA of 100 ng/ml or less.

An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a given (conformational) sequence in Fn amyloid-like FadA is an antibody that binds this epitope with greater affinity, avidity, more readily, and/or with greater duration than it binds to other epitopes. In embodiments of the antibodies or fragments, herein the antibodies or fragments preferentially bind Fn amyloid-like FadA. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibody subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia refers instead to the location of the structural loops (Chothia and Lesk, J. Mol. Biol. 196:901-917 (1987)). The AbM HVRs represent a compromise between the Kabat HVRs and Chothia structural loops and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

In embodiments, the variable regions disclosed herein are not modified. In embodiments, the invention encompasses modifications to the variable regions disclosed herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to Fn amyloid-like FadA. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table A, or as further described below in reference to amino acid classes, may be introduced and the products screened.

TABLE A

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a β-sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

A modification or mutation may also be made in a framework region or constant region to increase the half-life of an antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the fusion protein is produced in a eukaryotic expression system.

In an embodiment, the fusion protein produced in the eukaryotic expression system comprises glycosylation at a residue on the Fc portion corresponding to Asn297.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g., 2-[2-[3,5-bis(2-hydroxyethoxy) oxolan-2-yl]-2-(2-hydroxyethoxy)ethoxy]ethyl (E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

Administration can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, uretheral, and vaginal.

In embodiments, the antibody, fragment or fusion protein is administered at a dose of 0.5 mg/kg to 100 mg/kg. In embodiments, the antibody, fragment or fusion protein is administered at a dose of 101 mg/kg to 250 mg/kg. In embodiments, the antibody, fragment or fusion protein is administered at a dose of 251 mg/kg to 500 mg/kg. In embodiments, the antibody, fragment or fusion protein is administered at a dose of 501 mg/kg to 1000 mg/kg. In embodiments, the antibody, fragment or fusion protein is administered at a dose of 1001 mg/kg to 2000 mg/kg. In embodiments, the antibody, fragment or fusion protein is administered at a dose of up to 25 mg twice per daily, daily, every other day, weekly, monthly or every three months. In embodiments, the antibody, fragment or fusion protein is administered at a dose of 25 to 100 mg twice per daily, daily, every other day, weekly, monthly or every three months. In embodiments, the antibody, fragment or fusion protein is administered at a dose of 100 to 250 mg twice per daily, daily, every other day, weekly, monthly or every three months. In embodiments, the antibody, fragment or fusion protein is administered at a dose of 250 to 500 mg twice per daily, daily, every other day, weekly, monthly or every three months. In embodiments, the antibody, fragment or fusion protein is administered at a dose of 500 to 1000 mg twice per daily, daily, every other day, weekly, monthly or every three months. In embodiments, the antibody, fragment or fusion protein is administered at a dose of 1000 to 2000 mg twice per daily, daily, every other day, weekly, monthly or every three months.

A control value or a reference value of a parameter is a concept well-established in the art. For example, a reference value (a single value or a value range, for example) for the expression level of Fn amyloid-like FadA can be determined from one or more samples from, for example, unafflicted subjects, and can be normalized and/or matched as necessary.

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

Experimental Results

*Fusobacterium nucleatum* (Fn) is a Gram-negative oral commensal, prevalent in various human diseases. It is unknown how this common commensal converts to a rampant pathogen. We report here that Fn secretes an adhesin (FadA) with amyloid-like properties (Fn amyloid-like FadA) via the Fap2 autotransporter to enhance its virulence. The extracellular FadA binds Congo Red and Thioflavin-T, as well as antibodies raised against human amyloid β42. Fn produces amyloid-like FadA under stress and disease conditions, but not in healthy sites or tissues. It functions as a scaffold for biofilm formation, confers acid tolerance, and mediates Fn binding to host cells. Furthermore, amyloid-like FadA induces periodontal bone loss and promotes CRC progression in mice, with its pathological effects attenuated by amyloid-binding compounds. The uncleaved signal peptide of FadA is required for the formation and stability of mature FadA fibrils. Our study provides a link between periodontal disease and CRC, and indicates anti-amyloid therapies as interventions for Fn-mediated disease processes.

Fn Produces Amyloid-Like FadA Regulated by Growth Phase

Figures 1A, 1B, 1C:
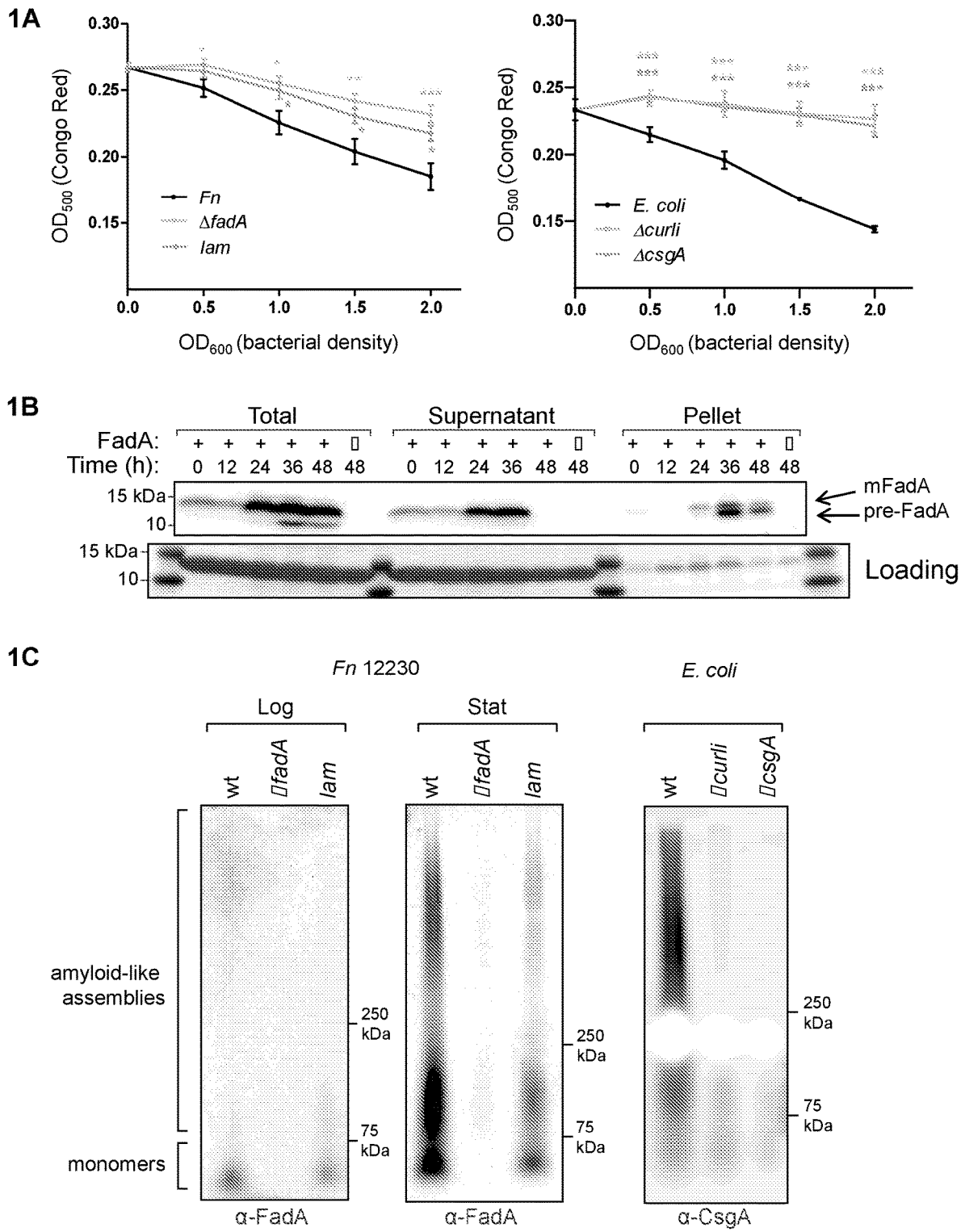
FIG. 1A-1F. Fn produces amyloid-like FadA in stationary phase. 1A. Congo Red depletion assay. Fn 12230 (black), the fadA-deletion mutant US1 (ΔfadA) (orange) and the spontaneous lam mutant (blue) (left panel) were grown to different OD600. *E. coli* MC4100, Δcurli, and ΔcsgA (right panel) were grown on TSA-blood agar plate at 26° C. for 48 hr. The bacteria were suspended in PBS to OD600 of 0.5, 1.0, 1.5 and 2.0, followed by incubation in 10 μg/ml Congo Red (CR) for 10 min. After centrifugation, the supernatants were measured at OD500. The results shown are the average of five independent experiments performed in duplicate. *p<0.05, p<0.01, *p<0.001 (compared to wild type, t-test). 1B. Kinetics of FadA production in Fn. Fn 12230 and US1 were inoculated to OD600=0.1. 10 OD600 units of bacteria were harvested by centrifugation at 12-hr intervals. Bacteria were lysed with 2 mg/ml lysozyme, followed by incubation in 1% sarkosyl at 4° C. for 20 minutes, which became the 'total' sample. Lysates were then centrifuged at 100,000 g for 20 minutes and the supernatants and pellets were collected. An aliquot of 5 µl is loaded onto each lane, followed by immunoblot using anti-FadA monoclonal antibody (mAb) 7H7 at 1:4,000 dilution to detect FadA protein in total, supernatant, and pellet fractions. Ponceau staining of lysozyme is shown as a loading control. Pre-FadA and mFadA are pointed by arrows. Note pre-FadA migrates faster than mFadA on SDS-PAGE as previously reported (Han et al., 2005). 1C. Analysis of detergent-resistant FadA polymers in wild-type Fn and its mutants by semi-denaturing detergent agarose gel electrophoresis (SDD-AGE) and Western blot analysis using mAb 7H7. Fn12230 (wt), fadA-deletion mutant US1 (ΔfadA) and spontaneous mutant lam (lam) were grown to log (OD600 0.3-0.4) or stationary phase (OD600>0.8), E. coli MC4100, Δcurli, and ΔcsgA were grown to stationary phase. The bacteria were harvested by centrifugation. Following sequential incubation in lysis buffer containing 2 mg/ml lysozyme and 1% sarkosyl, the insoluble pellets were obtained by centrifugation. An aliquot of 100 µg of each pellet was loaded onto 1.7% agarose gel followed by overnight electrophoresis in 0.5×TAE and 0.1% SDS. Following transfer to nitrocellulose membrane, Western blot was performed using mAb 7H7 at 1:4,000 dilution to detect the FadA proteins or anti-CsgA antibody at 1:15,000 dilution. The heterogeneously large detergent resistant FadA polymers were detected in wild-type Fn in the stationary phase, defective in US1 and lam, and absent in all in log phase. 1D. Immunohistochemical analysis of FadA in log and stationary phases. Fn12230 (Fn), fadA-deletion mutant US1 (ΔfadA) and spontaneous mutant lam in log and stationary phase were fixed before being placed onto glass slides and stained by mAb 7H7 at 1:800 dilution, followed by incubation of HRP-conjugated anti-mouse IgG and developed by DAB. The large FadA aggregates are detected specifically in wild-type Fn 12230 in the stationary but not in log phase. FadA was detected on lam, but without secreted aggregates. No FadA was detected in US1. The imagines were taken using 40× objective. Scale bar equals 20 µm. 1E. Double immunofluorescent staining of Fn2230, fadA-deletion mutant US1 (ΔfadA) and spontaneous mutant lam in log and stationary phases using mAb 7H7 at 1:800 dilution and anti-human β-amyloid polyclonal antibody A11 at 1:500 dilution, followed by incubation with Alexa Fluor 680-conjugated donkey anti-rabbit and Alexa Fluor 555-conjugated goat anti-mouse, both at 1:1,000 dilution. Co-staining of FadA and A11 was observed in Fn in stationary phase, not in log phase, or in US1 or lam. The imagines were taken under 60× objective. Scale bar equals 5 µm. 1F. Scanning electron microscopy of Fn 12230, US1 (ΔfadA) and lam in log and stationary phase at 10,000× magnification. Note the fibrous structure coating Fn in stationary phase, pointed by the clear arrows, but not in log phase. Scale bar equals 1 µm.

A distinctive property of amyloid and amyloid-like assemblies is their ability to bind amyloidophilic compounds such as Congo Red and Thioflavin-T (Evans et al, 2018; Tukel et al, 2009). To determine if Fn expresses amyloid-like FadA, we assessed whether Fn and its mutants bind Congo Red. Wild type Fn 12230 clearly bound Congo Red, depleting it from the solution in a density-dependent manner, while the fadA-deletion mutant US1 (ΔfadA) was defective (FIG. 1A). In order to compare with the well-characterized bacterial amyloid-like adhesin curli (Evans et al., 2018), wild-type curli-producing *E. coli* and curli mutants were tested in the same assay (FIG. 1A). The similarities observed between Fn and *E. coli* support that FadA is an amyloid-like adhesin.

Because Congo Red was depleted in a bacterial density-dependent manner, we conducted a kinetic analysis to examine production of amyloid-like FadA over the course of growth. Fn cultures were harvested and lysed at increasing time points following subculture and incubated with 1% sarkosyl. Resistance to ionic detergent is a characteristic of amyloid-like proteins (Sondheimer & Lindquist, 2000). Sarkosyl-resistant (i.e., amyloid-like) FadA (pellet) increased over time, and by 48 hours (late stationary phase), FadA was only detected in the pellet but not in supernatant, indicating the existence of FadA as predominantly insoluble aggregates (FIG. 1B). [On SDS-PAGE, pre-FadA migrates faster than mFadA (Xu et al., 2007).] This result indicates that although FadA is constitutively expressed in Fn, its molecular characteristics change during growth, and that production of FadA polymers is regulated by growth phase.

To examine the production of amyloid-like FadA aggregates, we employed semi-denaturing detergent agarose gel electrophoresis (SDD-AGE), followed by Western blot analysis using anti-FadA monoclonal antibody (mAb) 7H7. Amyloid-like (as opposed to amorphous or globular) assemblies are SDS-resistant and SDD-AGE allows for the resolution of these structures based on their size and resistance to the ionic detergent SDS. Fn produced massive and heterogeneously-sized amyloid-like FadA assemblies in stationary phase, similar as the curli-producing *E. coli*, but not in log phase (FIG. 1C). Our observation suggests FadA assembly could be regulated by nutrient depletion, a feature observed with other amyloid-like proteins (Berchowitz et al., 2015).

Figures 1D, 1E, 1F:
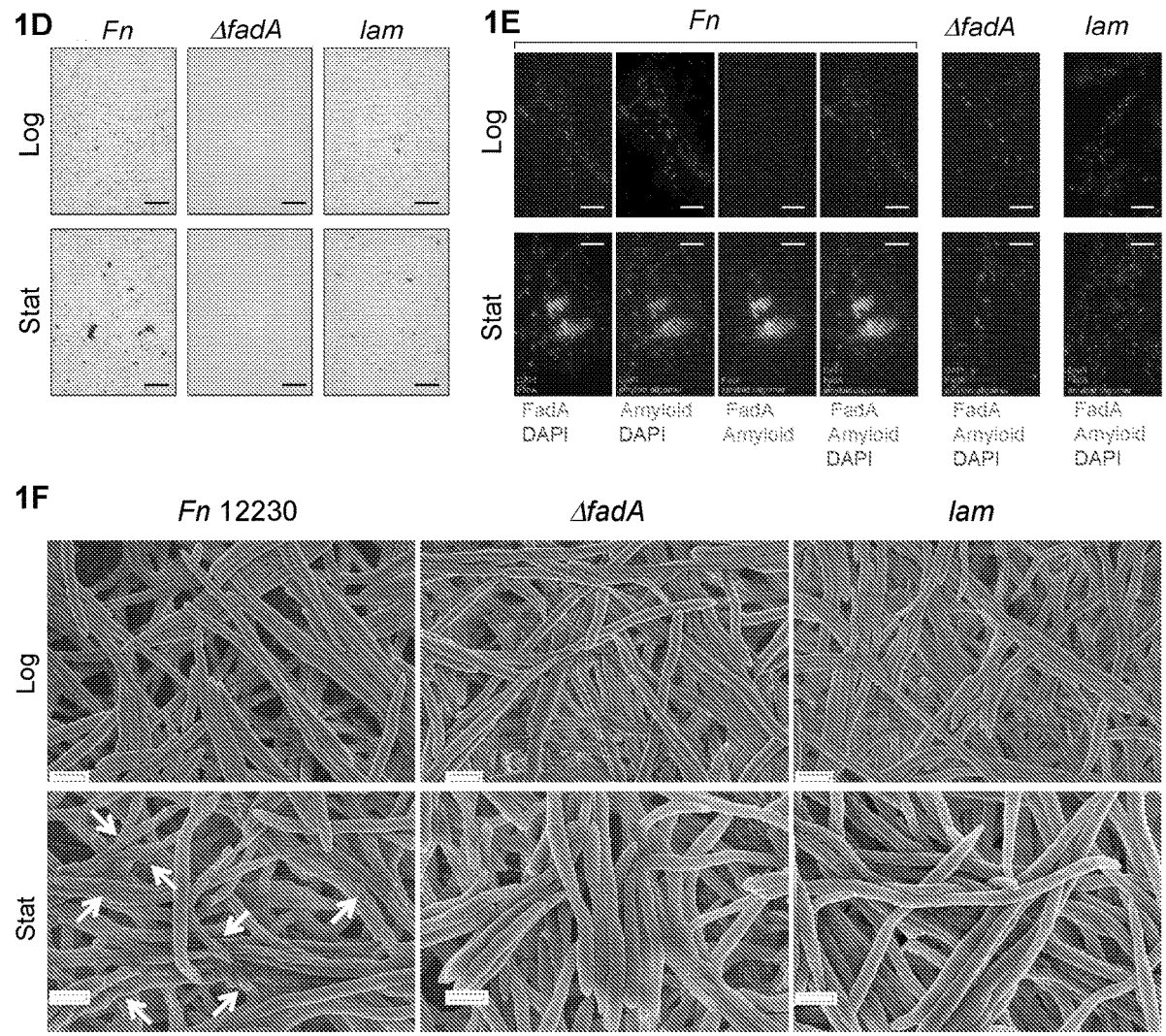

Image analyses were then conducted to visually examine the FadA aggregates. Increased secretion of FadA aggregates by wild-type Fn was detected by immunohistochemistry (IHC) in stationary phase compared to log phase (FIG. 1D). To further examine the amyloid-like properties of extracellular FadA aggregates, double immunofluorescent staining was performed using mAb 7H7 and polyclonal anti-human β-amyloid antibody A11, which specifically recognizes amyloid oligomers independent of amino-acid (aa) sequence. Co-staining between A11 and FadA was observed in stationary phase but not in log phase of wild type Fn (FIG. 1E). Scanning electron microscopy (SEM) confirmed the existence of extracellular "plaque-like" fibrils coating wild-type Fn in stationary phase, but not in log phase, which were significantly reduced in US1 (ΔfadA) (FIG. 1F). Together, these data confirm that Fn produces amyloid-like FadA as the bacteria enter stationary phase, possibly in response to nutrient deprivation.

Pre-FadA is a Key Component of Amyloid-Like FadA Secreted by Type V Autotransporter Fap2

FadA is an unusual adhesin in that it exists in two forms: a full-length peptide consisting of 129 aa residues (15.5 kDa), termed pre-FadA, and a cleaved "mature" form consisting of 111 aa residues (13.6 kDa) without the signal peptide, termed mFadA (FIG. 2A). Crystallographic analysis of mFadA reveals a filamentous structure, with predominantly α-helical monomers linked in a head-to-tail pattern through a "leucine chain" motif (Nithianantham et al., 2009). The mFadA alone exhibits little virulence, and pre-FadA by itself is insoluble under neutral pH. Together, these two forms constitute an active heterogeneous complex termed FadAc (Xu et al., 2007). Previous studies have demonstrated that recombinant FadAc, but not mFadA, is the active form for stimulating CRC growth (Fardini et al., 2011; Rubinstein et al., 2019; Rubinstein et al., 2013; Xu et al., 2007). FadAc is highly heterogeneous, with its size and function proportional to pre-FadA; with increasing pre-FadA, the multimeric complex becomes more heterogeneous, and the complex size and cell-binding activities also increase (Temoin et al, 2012a; Xu et al., 2007).

Using SDD-AGE and Western blot analysis using mAb 7H7, we found that FadAc expressed in *E. coli* also formed detergent-resistant polymers, although their sizes were smaller than those produced by Fn. In contrast, mFadA did not form polymers (FIG. 2B). These results indicate that while the full-size amyloid-like FadA polymers likely require additional factors and processes that are specific to Fn, FadAc has intrinsic capability to assemble into amyloid-like structure and that pre-FadA is a key component for amyloid formation.

To evaluate whether, and to what degree, FadA and its variants self-assemble into amyloid-like aggregates, we assessed binding of recombinant FadA proteins to two different antibodies that recognize amyloid structures: polyclonal anti-human amyloid-β antibodies OC and A11. The difference between these two antibodies is that A11 recognizes pre-fibril oligomers, while OC recognizes mature fibrils (Kayed et al, 2007). Only A11 is suitable for immunofluorescence staining, but both can be used for the analysis of purified proteins by slot blot. Among the recombinant FadA mutants tested, L14A and L76A did not produce pre-FadA (FIG. 8) and exhibited no filamentous structure or cell-binding function (Xu et al., 2007). These mutant proteins did not react with either OC or A11, similar as the negative control protein histone H1 (FIG. 2C, 8B). In contrast, FadAc, L-9A (carrying Leu-Ala mutation at position −9 in the signal peptide) and S71A reacted with both OC and A11, similar to the positive control protein Rim4, which readily forms β-sheet-rich amyloid-like aggregates (FIG. 2C, 8B) (Berchowitz et al., 2015). Previous study showed these latter group all retain filamentous structure and are functional (Temoin et al., 2012a). Interestingly, they all express both forms of FadA (FIG. 8A). Notably, mFadA reacted weakly with the anti-oligomer A11 but not with the anti-fibril OC, indicating that mFadA weakly forms oligomers, but not mature amyloid fibrils (compare FIG. 2C and FIG. 8A). This is consistent with observations of the crystal structure of mFadA, in which mFadA monomers link to one another in a head-to-tail manner to form a filament (Nithianantham et al., 2009). However, the mFadA filament is not resistant to SDS, as shown by the Thioflavin-T binding assay (FIGS. 2D & 2E).

FadA proteins that reacted with A11 or OC bound the amyloid-specific dye Thioflavin-T in a dose-dependent manner. Without SDS, mFadA bound more Thioflavin-T than FadAc at the same protein concentrations tested, possibly because more filaments are available for binding (FIG. 2D). However, mFadA did not bind Thioflavin-T in the presence of 0.1% SDS, while FadAc, L-9A and S71A all of which contained pre-FadA, bound Thioflavin-T. These results indicate that mFadA only forms the less stable oligomers but not fibrils, and that the signal peptide plays a critical role in the assembly of mature amyloid-like fibrils (FIG. 2E), consistent with the results of SDD-AGE (FIG. 2B). L14A, which does not form filamentous structure (Nithianantham et al., 2009) or react with A11 or OC (FIG. 2C and FIG. 8B), did not bind Thioflavin-T (FIG. 2D). The FadA proteins were also found to contain varying levels of β-sheets by circular dichroism (Table 1), a characteristic of amyloid proteins. Taken together, these data indicate that FadA proteins are capable to self-assemble into amyloid-like oligomers or fibrils.

To further investigate the role of pre-FadA in amyloid formation, we utilized a previously isolated spontaneous mutant, lam (for less adhesive mutant), which is defective in Fn autoaggregation, binding to host cells, and induction of IL8 (Han et al, 2000). The lam mutant was defective in producing pre-FadA but not mFadA (FIG. 2F). Consequently, it was severely defective in binding Congo Red (FIG. 1A), or producing large amyloid-like assemblies (FIG. 1C). Furthermore, IHC analysis showed that lam was defective in secreting FadA aggregates, but not bacterial surface FadA (FIG. 1D). It did not react with anti-amyloid antibody A11 by immunofluorescence staining (FIG. 1E), and lacked extra-cellular fibrils as determined by SEM (FIG. 1F). There observations support that pre-FadA is a critical component of amyloid-like FadA and is likely secreted.

DNA sequencing analysis of wild-type Fn 12230 and lam revealed two variations: (i) a 6-aa in-frame deletion in an open reading frame (ORF) sharing 62.3% identity to the Fap2 protein from Fn ATCC 23726, and (ii) a missense mutation (N284I) in a glycerol kinase homolog (Table 2). Fap2 is a Type V autotransporter required for Fn to interact with the immune cells and colonization in colorectal tumors (Abed et al, 2016; Coppenhagen-Glazer et al, 2015; Kaplan et al, 2010). It is possible that Fap2 is required for secretion of pre-FadA and/or the FadA polymers. Therefore, we analyzed Fn 23726 and its fap2 mutant in stationary phase by SDD-AGE and Western blot analysis. Similar to Fn 12230, Fn 23726 formed highly heterogeneous SDS-resistant FadA polymers while the fap2 mutant was almost completely defective (FIG. 2E). SDS-PAGE analysis showed mFadA levels remained constant in log and stationary phase in wild-type Fn 23726, while pre-FadA is significantly increased in stationary phase (FIG. 8C). The fap2 mutant was defective in producing pre-FadA regardless of growth phase, although mFadA was unaffected (FIG. 8C). These results demonstrate that the Fap2 autotransporter is required for secretion of pre-FadA, which is a critical component of the amyloid fibrils.

Amyloid-Like FadA is Detected in Periodontal Disease and CRC

Figure 3A:
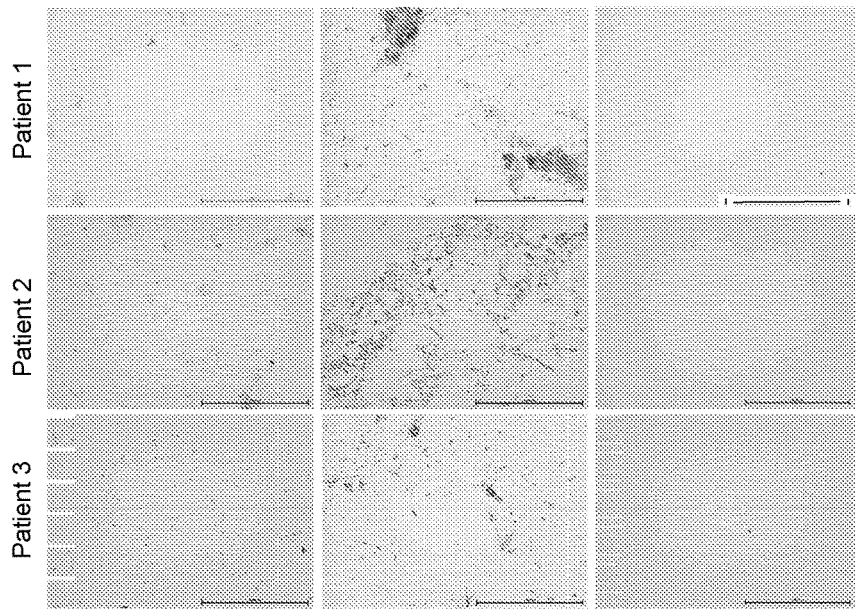
FIG. 3A-3B. Detection of amyloid-like FadA in periodontal disease and CRC. 3A. Detection of FadA in subgingival plaque samples by IHC. Three patients with periodontitis are shown here who provided plaque samples from their healthy sites (probing depth ≤3 mm, left panels) as well as periodontal disease sites (probing depth ≥7 mm, middle panels). IHC was performed as described using mAb 7H7 at 1:800 dilution. Anti-mouse IgG isotype control of the diseased site is shown (right panels). The images were taken using 100× objective. Scale bar equals 50 µm. 3B. Double immunofluorescence staining of paired normal and carcinoma tissues from two CRC patients. The frozen tissue sections were incubated with mAb 7H7 at 1:50 dilution and anti-amyloid antibody A11 at 1:25 dilution, or mouse and rabbit IgG control, followed by incubation with Alexa Fluor 555-conjugated goat anti-mouse and Alexa Fluor 680-conjugated donkey anti-rabbit, both at 1:1000 dilution. Co-staining of FadA (red) and amyloid oligomers (green) was observed in the carcinoma but not normal tissues. The images were taken under 60× objective. Scale bar equals 10 µm.
Figure 3B:
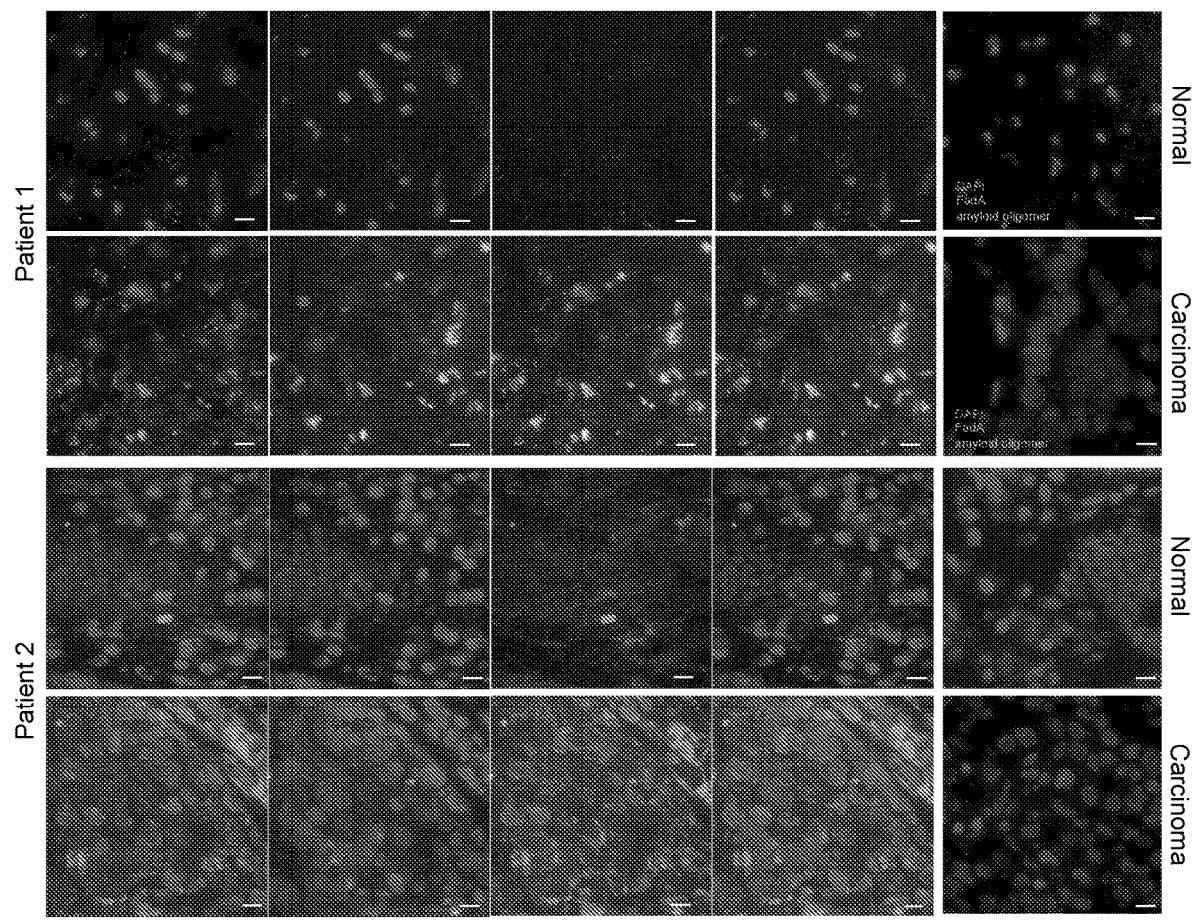

Our data indicates that not only does FadA assemble into an amyloid-like structure, but the formation of these structures is a regulated process. We hypothesize that the transition of FadA from monomers to amyloid-like fibrils substantiates Fn pathogenicity. Therefore, we examined the presence of amyloid-like FadA in periodontal disease and CRC. Previous studies have reported Fn and fadA gene levels are significantly increased in the colonic tissues and fecal microbiome of CRC patients, compared to the controls (Kostic et al, 2013; Rubinstein et al., 2013; Wirbel et al., 2019). Similarly, Fn 16S rRNA and fadA genes are also increased in periodontal diseased sites, compared to healthy subjects or healthy sites of periodontitis patients (FIG. 9). The increase is not only quantitative, but also qualitative, as FadA aggregates were detected in periodontal diseased sites but not in the healthy sites from the same patients (FIG. 3A). Consistently, amyloid-like FadA was detected in colorectal carcinoma tissues by fluorescent staining using A11, but not in the paired normal tissues (FIG. 3B). It should be noted that since OC is not suitable for immunofluorescent staining, A11 was used, which was less ideal because it captures the oligomeric seeds rather than the mature fibrils. This could partially explain the incomplete overlap staining of A11 and anti-FadA 7H7. Nonetheless, the overlap staining was only observed in the carcinoma tissues, but not in the matched normal controls. The potential pathogenicity of amyloid-like FadA was then assessed in a series of in vitro and in vivo tests.

Amyloid-FadA Facilitates Biofilm Formation

Figures 4A, 4B, 4C, 4D, 4E, 4F:
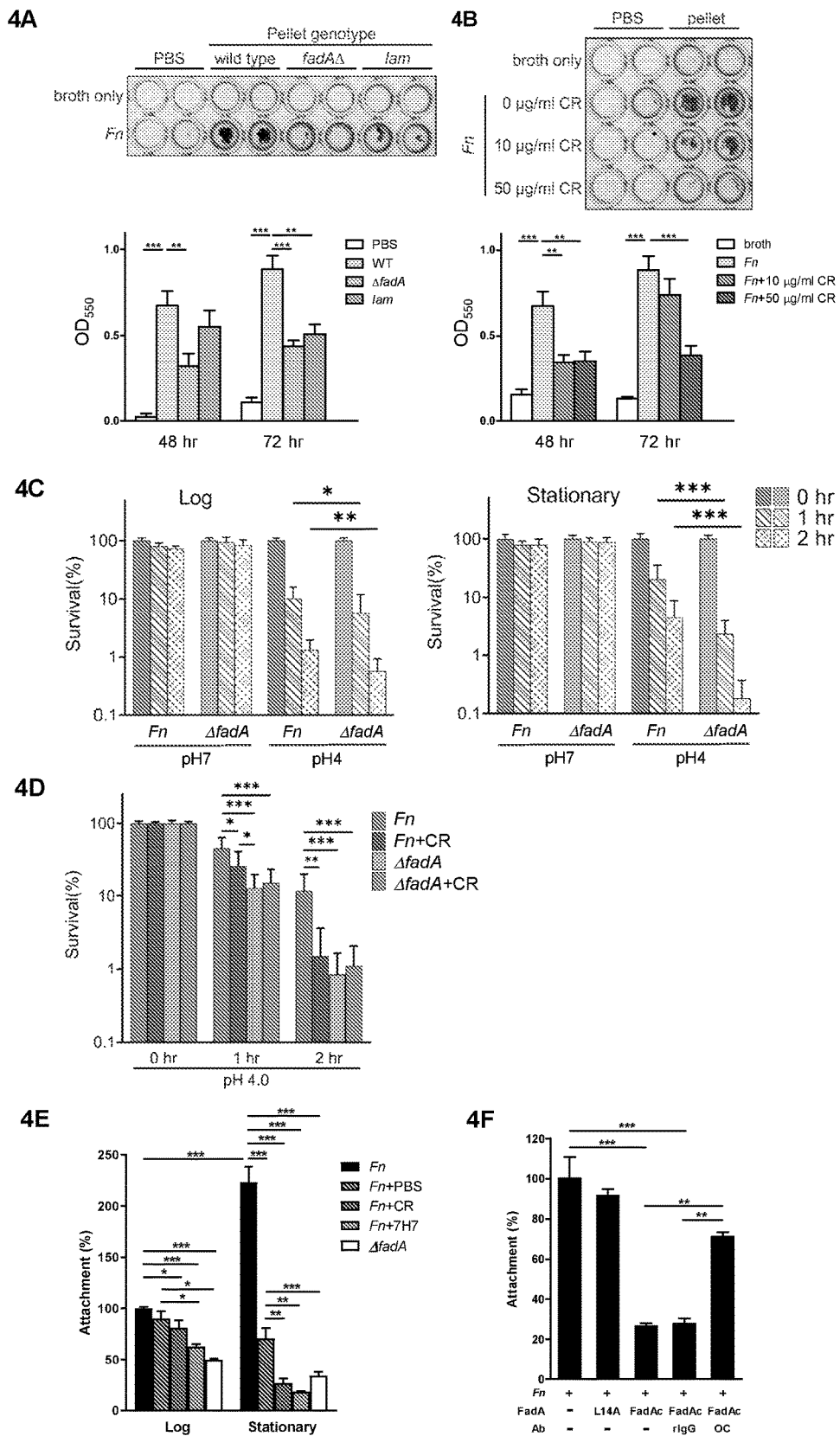
FIG. 4A-4F. Functional analysis of amyloid-like FadA in vitro. 4A. Facilitation of Fn biofilm formation by amyloid-like FadA. An aliquot of 10 µg each of the detergent-resistant pellets prepared from of Fn 12230 (wild type), US1 (ΔfadA) and lam, or PBS, was added to the 96-well plates and incubated at 37° C. for 5 hours. Fresh culture of Fn 12230 was diluted to OD600 of 0.2 and an aliquot of 200 µl was added to the wells, followed by incubation at 37° C. for 48 or 72 hours under anaerobic conditions. Following washes, the biofilms were incubated with 100 μl 0.1% crystal violet for 15 min. After washing, 100 μl 95% ethanol was added to each well and the optical density at OD550 was measured in a microplate reader. The results shown are the average of four experiments each performed in duplicate. A representative image following 72 hours of incubation is shown in the top panel. $p<0.01$. *$p<0.001$ (t-test). 4B. Inhibition of biofilm formation mediated by detergent-resistant Fn pellets by Congo Red. An aliquot of 10 μg detergent-resistant pellets prepared from Fn 12230 (pellet) was added in 96-well plates in the presence of 0, 10 or 50 μg/ml Congo Red (CR), followed by addition of Fn 12230 and incubated as described above. The results shown are the average of four experiments each performed in duplicate. A representative image following 72 hours of incubation is shown in the top panel. $p<0.01$, *$p<0.001$ (t-test). 4C. Effects of pH on Fn survival. Wild type Fn 12230 (Fn) or its fadA deletion mutant US1 (ΔfadA) grown to log or stationary phase were washed and incubated in PBS at pH 7 or pH 4 for 1 or 2 hours. The live bacterial counts at time 0 were designated as 100%, and those after 1 or 2 hrs of incubation were expressed relative to time 0. The results shown are the average of 5 (for log) or 4 (for stationary) independent experiments, each performed in triplicate. *$p<0.05$, $p<0.01$, *$p<0.001$ (One-way ANOVA). 4D. Effects of Congo Red on Fn survival in acidic environment. Wild type Fn 12230 (Fn) or its fadA deletion mutant US1 (ΔfadA) grown to stationary phase were washed and incubated in PBS at pH4 in the presence of absence of 50 μg/ml Congo Red (CR) for 1 or 2 hours. The live bacterial counts at time 0 were designated as 100%, and those after 1 or 2 hrs of incubation were expressed relative to time 0. The results shown are the average of 5 independent experiments, each performed in duplicate. *$p<0.05$, $p<0.01$, *$p<0.001$ (One-way ANOVA). 4E. Attachment of Fn 12230 grown to log or stationary phase to CRC cells DLD1. Fn 12230 (Fn) was either unwashed or washed twice with PBS or 1 mg/ml Congo Red (CR), or mixed with 20 μl mAb 7H7, before adding to the monolayers at multiplicity of infection (MOI) of 50:1. US1 (ΔfadA) was included as a negative control. The attachment level by untreated log phase Fn was designated as 100%, which all other values were expressed relative to. Data shown are mean values±SEM. The experiment was performed in duplicate and repeated four times. *$p<0.05$, $p<0.01$, *$p<0.001$ (t-test). 4F. Inhibition of Fn attachment by FadAc in the presence or absence of anti-amyloid antibody OC. An aliquot of 50 μg purified recombinant FadAc was pre-incubated with DLD1 for 45 min either alone, or mixed with 20 μl OC or rabbit IgG control, before Fn was added and the attachment assay performed as above. The attachment value by Fn alone was designated as 100%, with all other values expressed relative to it. FadA mutant L14A was included as a negative control. Data shown are mean values SEM. The experiment was performed in duplicate and repeated three times. *$p<0.05$, **$p<0.01$ (One-way ANOVA).

In both periodontal disease and CRC, biofilms play important roles, allowing bacteria to secure colonization in the host, resist host immune defense, and acquire nutrients from other members of the microbial community (Tomkovich et al, 2019). We hypothesize that amyloid-like FadA may serve as a scaffold for biofilm formation. Sarkosyl-insoluble pellets were obtained from Fn 12230, US1 (ΔfadA), and lam by differential centrifugation as described above, and were used to coat 96-well plates, followed by inoculation of Fn12230 (experimental scheme outlined in FIG. 10A). Fn 12230 by itself did not form biofilm under the test conditions, possibly due to insufficient secreted FadA. Sarkosyl-resistant pellets purified from wild-type Fn readily facilitated biofilm growth, but the sarkosyl-insoluble pellets obtained from US1 (ΔfadA) and lam were defective in facilitating biofilm formation (FIG. 4A). These results indicate that secreted amyloid-like FadA support biofilm growth in trans, independent of surface-expressed FadA. Notably, the sarkosyl-resistant pellet obtained from US1 (ΔfadA) supported partial biofilm formation, thus, within the total amyloid-like assemblies produced by Fn, FadA itself plays a primary role, but additional components may also contribute to the scaffold. For example, genome sequence of Fn 12230 revealed two additional FadA homologs, FadA2 and FadA3, with 24.5% and 25% identity with FadA, respectively (Table 3). This is consistent with previous reports of detecting multiple copies of fadA genes on the *Fusobacterium* genomes and may explain some of the residual activities observed in US1 (ΔfadA) (Manson McGuire et al, 2014; Umana et al., 2019).

To confirm it was indeed the amyloid-like FadA that promoted biofilm formation, we repeated the experiment in the presence of Congo Red (scheme detailed in FIG. 10A), which has been used to disrupt and inhibit the cytotoxicity associated with amyloid-like polyglutamine aggregates (Sanchez et al, 2003). Congo Red inhibited biofilm formation in a dose-dependent manner (FIG. 4B), without affecting the viability of Fn (FIG. 10C).

Amyloid-Like FadA Confers Acid Tolerance

Since Fn and fadA are detected in the fecal microbiome, it indicates the microorganism travels through the GI tract (Thomas et al., 2019; Wirbel et al., 2019). We speculate that secreted amyloid-like FadA may serve as a protective "shield" facilitating Fn survival in the acidic gastric environment (see FIG. 1F). Although the survival of wild-type Fn at neutral pH (7.0) was indistinguishable between the two growth phases, increased survival in stationary phase was observed compared to log phase in acidic pH (4.0) (FIG. 4C, compare the grey bars between left and right panels). Furthermore, when compared to US1 (ΔfadA), survival of wild-type Fn was dramatically better in stationary phase than in log phase at pH 4.0 (FIG. 4C).

To determine whether and to what extent amyloid-like FadA plays a role in the observed acid-resistance of Fn, the viability of wild type and US1 (ΔfadA) in stationary phase at pH 4.0 was tested in the presence or absence of Congo Red. Remarkably, Congo Red drastically reduced viability of wild-type Fn to the similar levels as US1, without affecting US1 (ΔfadA), indicating that the FadA-mediated acid-resistance relies solely on its amyloid-like properties (FIG. 4D).

Amyloid-Like FadA Facilitates Fn Binding to CRC Cells

Fn binding to human CRC cells DLD1 increased by ~2.5-fold in stationary phase compared to log phase (FIG. 4E). Furthermore, while washing the bacteria with PBS or Congo Red had little or no effect on binding in log phase, it reduced binding in stationary phase by ~2.5 and 5-fold, respectively (FIG. 4E). These results indicate that the secreted amyloid-like assemblies are of critical importance for the ability of Fn to bind CRC cells. Furthermore, anti-FadA mAb 7H7 only mildly inhibited Fn binding in log phase, but dramatically inhibited in stationary phase, supporting that the enhanced binding in stationary phase was mediated by FadA (FIG. 4E). These results are consistent with previous observations that Fn binds CRC cells and promotes tumor progression through FadAc (Rubinstein et al., 2019; Rubinstein et al., 2013). When DLD1 cells were pre-incubated with FadAc, Fn binding was effectively inhibited. However, when FadAc was pre-incubated in the presence of anti-amyloid antibody OC, the inhibitory activity of FadAc was significantly reduced, while the rabbit IgG control had no such effect (FIG. 4F). These results demonstrate that the amyloid properties of FadAc are critical to mediate Fn binding to CRC cells.

Amyloid-Like FadA Facilitates Fn Colonization and Stimulation of CRC In Vivo

To examine the role of amyloid-like FadA in CRC progression in vivo, a mouse xenograft model was used. Consistent with the in vitro observations, Congo Red significantly inhibited Fn colonization in xenograft tumors (FIG. 5A). To determine if amyloid-like FadA is a driver of CRC progression, wild-type Fn 12230, US1 (ΔfadA) and lam were injected into xenograft tumors in nude mice. Fn 12230 significantly stimulated tumor growth while US1 (ΔfadA) and lam were defective (FIG. 5B). The fadA-complementing strain USF81 restored tumor growth to similar levels as Fn 12230 (FIG. 11). These results demonstrate that the secreted amyloid-like FadA is required for promoting tumor progression. We have shown previously that FadAc, but not mFadA, stimulated xenograft tumor growth (Rubinstein et al., 2013). The effect of FadAc on xenograft CRC tumors was assessed in the presence or absence of the OC antibody. Compared to rabbit IgG control, the OC antibody significantly attenuated FadAc-mediated tumor growth (FIG. 5C). Similarly, the sarkosyl-resistant pellets prepared from wild-type Fn significantly stimulated tumor growth compared to the pellets of US1 (ΔfadA), but the enhanced stimulation was completely attenuated by the OC antibody (FIG. 5D). Together, these results elucidate the critical role of amyloid-like FadA in promoting CRC progression.

Amyloid-Like FadA Induces Periodontal Bone Loss in Mice

To assess the virulence potential of amyloid-like FadA in periodontal disease, a mouse periodontitis model was established. Fn 12230, US1 (ΔfadA) and lam were inoculated continuously into the oral cavity of C56BL/6 mice for 10 weeks. Significant periodontal bone loss was detected in the molars of mice treated with Fn 12230, but not in those treated with US1 (ΔfadA) or lam (FIG. 6, 12). These results demonstrate that secreted amyloid-like FadA plays a key role in inducing periodontal bone loss.

Discussion

Fn is an abundant commensal bacterium dwelling in the oral flora of both periodontal healthy and periodontal disease-affected individuals. It is present in gingivitis, a reversible form of periodontal disease, but also in more severe forms of periodontitis where irreversible tissue damages occur. Once outside the oral cavity, Fn causes infections that are often life threatening. The motivation of this study was to determine how this bacterium functions both as a ubiquitous oral commensal and a rampant systemic pathogen. Here, we show that the virulence factor FadA undergoes a dramatic biochemical transformation into an amyloid-like structure to enhance its virulence potential. The amyloid-like FadA exhibits common amyloid properties such as binding to amyloid dyes Congo Red and Thioflavin-T, resistance to ionic detergents, and formation of large heterogeneous filamentous aggregates. In addition, it reacts with antibodies raised against human amyloid β42, which shares no primary sequence homology with FadA. The emergent amyloid-like properties of FadA facilitate several critical pathogenic attributes that ultimately allow Fn to survive under stressful conditions, form biofilms, bind host cells, colonize CRC tumors, stimulate CRC progression and induce periodontal bone loss. In particular, the enhanced virulence can be inhibited by the amyloid dyes or the anti-amyloid antibodies, indicating the critical role of the amyloid properties in pathogenesis. Amyloid-like FadA is specifically enriched in diseased periodontal sites and in colonic carcinomas, but not in the non-diseased controls, supporting that amyloid-like FadA may serve as a molecular switch for the commensal-to-pathogen conversion. Alternatively, expressing of amyloid-like FadA could also be an adaptive response to the changing environment, which then enhances the virulence potential of Fn. These two scenarios are not mutually exclusive, similar to the positive feedback interactions between FadA and Annexin A1 in CRC (Rubinstein et al., 2019).

Fn has long been recognized as an essential component of subgingival biofilm. The discovery of amyloid-like FadA as a scaffold sheds mechanistic light on the critical role of Fn in dental plaque development. Furthermore, our data from the mouse periodontitis model indicates that Fn plays more than just a scaffolding role in periodontal disease; instead, it is actively involved in the disease process. Our results clearly demonstrate that amyloid-like FadA, rather than FadA monomers, is the key driver of pathogenesis, not only in periodontal disease, but also in CRC progression. Recent studies have linked periodontal disease to CRC (Kim et al, 2019). The causal role of amyloid FadA in both periodontal disease and CRC provides a possible mechanistic link between these two diseases. Elevated amyloid-like FadA in periodontal disease sites may facilitate systemic dissemination of Fn thus increasing the risk for developing systemic infections such as pregnancy complications as well as cancer.

The current study reveals that in the presence of amyloid FadA, Fn could survive the acidic environment and disseminate through the GI tract. While Fn can also disseminate via circulation, the saliva, which contains high titers of bacteria, is constantly being swallowed, providing a means for GI dissemination. Findings of significantly increased Fn and fadA in the fecal microbiome of CRC patients are consistent with the GI translocation (Thomas et al., 2019; Wirbel et al., 2019). Oral inoculation of Fn stimulated colonic tumor formation in mice (Kostic et al., 2013; Rubinstein et al., 2019). We note that bacterial conglomerates, as they are in saliva, could be even more resistant to acidic environment than a singular species in planktonic broth. We have recently demonstrated that the Fusobacteria communities in stomach and colon share more similarities, with their community diversities significantly reduced compared to in saliva (Richardson et al, 2020). It is plausible that Fn strains expressing elevated amyloid-FadA may have selective advantage during transmission, through either circulation or the GI tract. Identification of amyloid-producing Fn may help identify individuals at risk for developing diseases implicated by Fn.

It should be pointed out that acid tolerance is not only beneficial to the bacteria during GI translocation, but also help their survival in the tumor microenvironment. Due to increased glycolysis in cancer, high levels of lactate are secreted, leading to acidic extracellular environment (Jiang, 2017). The enhanced colonization and growth stimulation of CRC by amyloid FadA may be due to a combination of enhanced biofilm formation, acid tolerance, and binding to the cancer cells.

Previous studies showed that pre-FadA is required for FadA function (Temoin et al, 2012b; Xu et al., 2007). We now discover that it is a key component of amyloid-like FadA, required for the formation of mature fibrils. It is unclear if pre-FadA alone, or a mixture of pre-FadA and mFadA, is present in the secreted amyloid-like FadA. We speculate that the mFadA filaments observed in the crystal structure could be intercalated with pre-FadA. The highly hydrophobic signal peptides from two neighboring filaments may form anti-parallel β-sheets serving as "hooks" to link the filaments, stacking multiple FadA filaments into fibrous structure (FIG. 7). This model is similar to the phenol-soluble modulin α3 (PSMα3) peptide secreted by *Staphylococcus aureus*, which forms amyloid-like fibrils with α-helices stacked perpendicular to the fibril axis (Tayeb-Fligelman et al, 2017). Such an amyloid "lattice" is consistent with the plaque-like coating we observe on Fn. This model explains all the observations we have made with FadA so far. We have reported previously that FadAc, but not mFadA, is the active form, and that the size and function of FadAc is proportional to the amount of pre-FadA in the complex (Temoin et al., 2012b; Xu et al., 2007). As shown in our model, pre-FadA plays a crucial role in the formation of mature fibrils. With increasing quantities of pre-FadA, more singular FadA filaments crosslink with one another, thus forming increasingly large, heterogeneous and stable fibrous structure. Without pre-FadA, each FadA oligomer filament can be easily dissociated. This could explain the instability of mFadA, which was unable to bind Thioflavin-T in the presence of SDS, while FadAc and the mutants that retained pre-FadA did.

The finding that amyloid-like FadA is secreted via the autotransporter Fap2 is unexpected and intriguing. Since the Fap2 mutants are defective in producing pre-FadA, without affecting mFadA, Fap2 may be required for secreting pre-FadA and/or amyloid-like FadA. Fap2 mutants have been found to be defective for colonizing murine placentas and colorectal tumors, similar as the fadA-deletion mutant (Abed et al., 2016; Coppenhagen-Glazer et al., 2015). It is plausible that some effects exhibited by the Fap2 mutant may be due to lack of amyloid-FadA. Since wild-type Fn produces significantly larger polymers than *E. coli* expressing FadA, additional bacterial components may be involved in the fibril formation and/or secretion.

Unveiling the significance of amyloid-like FadA in Fn pathogenesis opens new doors for therapies. CRC implicated with Fn often has poor prognosis, due to its activation of the oncotarget Annexin A1, induction of chemo-resistance and stimulation of metastasis (Bullman et al, 2017; Casasanta et al, 2020; Mima et al, 2016; Rubinstein et al., 2019; Yu et al, 2017). However, the use of broad-spectrum antimicrobials to treat cancer is undesirable due to disturbance of the entire flora. A specific therapy against Fn virulence factors may be more effective. Our results suggest that targeting amyloid-like FadA could substantially and specifically inhibit the pathogenic potential of Fn in multiple diseases. While Congo Red is very unlikely to be useful due to its carcinogenicity, the anti-FadA antibody 7H7 and many other anti-amyloid compounds, such as those inhibiting polymerization of the curli fibers produced by *E. coli* (Cegelski et al, 2009), present untapped potential as anticancer agents. Some anti-amyloid drugs that have failed as treatments for neurodegenerative disease because of the immense challenge of traversing the blood-brain barrier could have previously unexpected utility against Fn-driven CRC and other debilitating diseases. Since FadA is uniquely encoded by *Fusobacterium* (Han et al., 2005), it is an ideal therapeutic target to specifically inhibit Fn-mediated pathogenesis.

In summary, we present evidence that Fn regulates its virulence by controlling the production of amyloid-like FadA. With increasing evidence of commensal microbes turning pathogenic in various human diseases, the discovery that Fn secretes an amyloid-like adhesin to enhance its pathogenicity represents a novel paradigm. Furthermore, the discovery that an amyloid-like bacterial protein promotes both periodontal disease and tumorigenesis not only sheds remarkable new lights on how oral health could impact extra-oral infections, but also broadens the scope for therapeutic development for a variety of human diseases.

Materials and Methods

Bacterial strains and cell cultures. The bacterial strains used in this study are listed in Table 4. Fn strains were grown as described (Han, 2006). Human CRC cells DLD1 were maintained as previously described (Rubinstein et al., 2019; Rubinstein et al., 2013). *E. coli* MC4100, Δcsg, and ΔcsgA were kindly provided by Dr. Matthew Chapman at University of Michigan.

Congo Red depletion assay. Fn 12230, US1(ΔfadA) and lam were grown to stationary phase, followed by resuspension in PBS to OD600 of 0.5, 1.0, 1.5 and 2.0. Five microliters of 2 mg/ml Congo Red (Sigma-Aldrich CAT #C6277) was added to 1 ml bacterial suspension to reach a final concentration of 10 μg/ml and incubated at room temperature for 10 min. The bacterial suspensions were centrifuged at 10,000 g for 5 min. An aliquot of 200 μl of supernatant was transferred to a 96-well plate to measure OD500 in a microplate reader. Each experiment was performed in duplicate and repeated four times.

Semi-denaturing detergent agarose gel electrophoresis (SDD-AGE). Fn 12230, Fn 23726 and their respective mutants were grown to 0.3-0.4 OD600 (log phase) or >0.8 OD600 (stationary phase). Recombinant *E. coli* BL21 expressing FadAc or mFadA were grown to 0.6 OD600, followed by induction with 1 mM IPTG for 3 hours. *E. coli* MC4100, Δcurli and ΔcsgA were grown for 48 h at 26° C. on YESCA plates. The bacteria were then collected by centrifugation at 5,000 g for 5 min, and lysed by incubation in the lysis buffer (10 mM Tris pH8.0, 0.1 M NaCl, 0.1 mM EDTA, 0.5% Triton X-100, and 2 mg/ml lysozyme) at 40° C. for 20 min with rotation. Sarkosyl was then added to a final concentration of 1% and incubated at 40° C. for 20 min with rotation. The samples were centrifuged at 18,000 g at 40° C. for 20 min. After measuring the protein concentrations by BCA, the pellets were stored at −80° C. until use. An aliquot of 50 μg (for *E. coli*, Fn 23726 and its mutants) or 100 μg (for Fn 12230 and its mutants) of the pellets prepared above were incubated with 4× loading buffer [0.5×TAE (20 mM Tris pH 8.3, 20 mM acetic acid, 0.5 mM EDTA), 8% SDS, 20% glycerol, bromophenol blue] for 10 min before loading onto 1.7% agarose gel containing 0.5× TAE and 0.1% SDS. The electrophoresis was carried out overnight at 40 C with circulating 0.5×TAE containing 0.1% SDS. Components on the gel were then immobilized onto nitrocellulose membrane by capillary transfer in TBS (50 mM Tris-HCl, 150 mM NaCl pH 7.4) for 24 hours at room temperature, followed by Western blot analysis (see below).

Western-blot analysis. One milliliter each of Fn 12230, US1 and lam in stationary phase was pelleted by centrifugation, and loaded onto 12% SDS-PAGE. Following electrophoresis, the bacterial components were transferred to PVDF membranes (Bio-Rad, Hercules, CA). The membrane was blocked with 5% skim milk in TBS containing 0.1% Tween 20 (TBST) at room temperature for 1 hour followed by incubation with anti-FadA monoclonal antibody (mAb) 7H7 at 1:4000 dilution in 0.5% skim milk in TBST at 4° C. overnight. After washing three times with TBST, the membrane was incubated with HRP-conjugated goat-anti-mouse IgG at 1:4,000 dilution in TBST at room temperature for 1 hour. Following washes, the immune-reactive components were detected with ECL Western Blotting Substrate (Thermo Fisher Scientific).

Time course study. Fn 12230 and US1 were sub-cultured to OD600 of 0.1 and grown in Columbia Broth supplemented with 5 μg/ml hemin and 1 μg/ml menadione at 37° C. under anaerobic conditions. Ten OD600 units of bacteria were harvested by centrifugation at 12-hr intervals, followed by centrifugation at 5,000 g for 5 min. The bacteria were lysed with 500 μl lysis buffer containing 2 mg/ml lysozyme at 40° C. for 20 min with rotation, followed by addition of sarkosyl to a final concentration of 1% and incubated at 4° C. for 20 min with rotation. An aliquot of 30 μl homogeneous mixture was saved as "Total" sample. The remaining mixture was centrifuged at 100,000 g for 20 min at 4° C. An aliquot of 30 μl supernatant was saved as "Supernatant". The pellet was resuspended in 470 μl lysis buffer, and an aliquot of 30 μl was taken as "Pellet" sample. The samples were then analyzed by Western blot analysis as described above. Ponceau staining of lysozyme was used as a loading control.

Slot blot assay. Ten micrograms each of purified recombinant protein was slot-blotted onto nitrocellulose membrane (BioRad) and assayed for reactivity with polyclonal anti-amyloid fibril antibodies OC (α-amyloid fibril OC, Sigma-Aldrich CAT #AB2286) at 1:5,000 dilution and goat-anti-rabbit IgG (GE Healthcare) at 1:10,000 dilution, or polyclonal anti-amyloid oligomer antibody A11 (α-oligomer A11 at 1:5,000 dilution, ThermoFisher Scientific CAT #AHB0052) and goat-anti-rabbit IgG at 1:10,000 dilution, followed by detection with ECL Prime (GE Healthcare). Amyloid-like recombinant Rim4 was used as a positive control (Berchowitz et al., 2015) and histone H1 was used as a negative control. Loading was assessed by Ponceau stain (Sigma CAT #P7170).

Thioflavin-T binding assay. Thioflavin-T assay was conducted as previously described (Tukel et al., 2009). A mixture of 50 μl of FadA proteins and 50 μl of 10 μM Thioflavin-T was added to a black 96-well plate and incubated for 10 min at room temperature. After incubation, the fluorescence intensity was determined using a SpectraMax M5 microplate reader at excitation wavelength of 440 nm and emission wavelength of 500 nm. For SDS stability test, the FadA proteins were pre-incubated in 0.1% SDS for 30 min at room temperature, followed by Thioflavin-T binding assay as described above.

Immunohistochemistry (IHC). Bacteria and dental plaque samples were fixed in 4% paraformaldehyde, resuspended in PBS and placed on electro-charged slides. Endogenous peroxidase was quenched in 3% hydrogen peroxide for 30 min, followed by washing. Slides were incubated with 5% skim milk for 1 hour at room temperature, followed by anti-FadA mAb 7H7 raised against FadAc at 1:800 dilution or mouse IgG isotype control (R&D Systems, Minneapolis, MN) overnight at 40° C. After washing, slides were blocked in 2.5% horse serum for 1 hour at room temperature and incubated with ImmPRESS HRP anti-mouse IgG (Vector Lab) for 30 min at room temperature followed by washes, before being developed with the DAB Peroxidase Substrate Kit (Vector Lab), counter stained hematoxylin, dried by sequential incubation in 70%, 95%, 100% ethanol and xylene, and covered in Permount mounting medium (Fisher chemical).

For formalin-fixed paraffin embedded (FFPE) mouse xenograft tumors, the slides were incubated at 60° C. for 1 hour, and de-paraffinized by incubation in xylene for three times, followed by rehydration with sequential incubation in 100%, 95%, 70% ethanol, ddH$_2$O and PBS. Endogenous peroxidase was quenched in 3% hydrogen peroxide for 15 min, followed by washing. Slides were incubated with 2.5% horse serum in PBS containing 0.5% BSA for 2 hours at room temperature, followed by anti-Fn polyclonal antibodies at 1:500 dilution or rabbit IgG isotype control (Invitrogen) overnight at 40° C. After washing, slides were incubated with ImmPRESS HRP anti-rabbit IgG (Vector Lab) and developed as described above.

Double-immunofluorescent staining. Bacterial cells were fixed, washed with PBS and placed on slides followed by incubation with 3% hydrogen peroxide and 5% skim milk as described above. Slides were incubated with anti-FadA mAb 7H7 antibody at 1:800 dilution and anti-amyloid oligomer antibody A11 (ThermoFisher Scientific CAT #AHB0052) at 1:500 dilution or mouse IgG (R&D Systems, Minneapolis, MN) and rabbit IgG isotype (Invitrogen) controls overnight at 40° C. After washing, slides were incubated with Alexa Fluor 680-conjugated donkey anti-rabbit (Invitrogen) at 1:1,000 dilution and Alexa Fluor 555-conjugated goat anti-mouse (Invitrogen) at 1:1,000 dilution, washed and covered in mounting medium containing DAPI.

For human colonic specimens, frozen tissue sections were fixed in 4% paraformaldehyde for 15 min, sequentially washed by 70% ethanol, ddH$_2$O and PBS, and permeabilized by 0.1% Triton X-100 in PBS followed by blocking in 5% skim milk. Slides were incubated with α-FadA mAb 7H7 antibody at 1:50 dilution and α-amyloid antibody A11 at 1:25 dilution, or mouse and rabbit IgG controls, overnight at 40° C. Then slides were washed, incubated with secondary antibodies as described above.

Scanning Electron Microscope (SEM). Bacteria cultures were harvested by gentle centrifugation, washed in PBS, re-suspended in 2% (v/v) glutaraldehyde in PBS and fixed for one hour at 4° C. Bacteria were fixed again by 1% osmium tetroxide in PBS for one hour at 4° C. Fixed bacteria were dehydrated with 25%, 50%, 75% and 100% ethanol, then dried with the Critical Point Dryer (CPD) to remove ethanol. Before imaging, samples were coated with Au/Pd to be electrical conductive during electron microscopy. Zeiss Sigma VP SEM instrument was used at an operating voltage of 3 kV with an InLense detector to obtain more surface information of the bacteria exterior. ThermoFisher/FEI Talos F200×FEI instrument operating at 200 kV was also utilized to observe both interior and exterior of bacteria at higher magnifications.

Bacterial genome sequencing and variation identification. Fn12230 and 1am DNA was extracted using modified protocol of the Qiagen MagAttract PowerMicrobiome DNA/RNA Kit (Qiagen 27500-4-EP). To obtain the genome reference of Fn strain, paired-end library was prepared based on a low-volume Nextera sequencing protocol (Baym et al, 2015) and sequenced on Illumina HiSeq 4000 or HiSeq X platform to generate more than 3 million paired-end reads for each sample. Raw reads were then processed by Cutadapt v2.1 with following parameters "--minimum-length 25:25 -u 15 -u -5 -U 15 -U -5 -q 15 --max-n 0 --pair-filter=any" to remove low-quality bases and Nextera adapters. PacBio long-read sequencing was performed for the reference strain Fn 12230 by SNPsaurus to improve the performance of de novo genome assembling. Illumina reads passing quality filtering and PacBio long reads were assembled using Unicycler with hybrid mode to generate the genome sequence of reference strain and the genome were then annotated using Prokka v1.13.3 with parameter "--rnammer -rfam". A complete genome of Fn 12230 (2.42 Mbp) and two circular plasmids (46.3 Kbp and 5.85 Kbp) was obtained. To identify the genomic variation of 1am, the reads obtained with 1am were aligned to the assembled reference genome using Bowtie2 v2.3.4 in paired-end mode with default setting. Resulting reads alignments were then processed by SAMtools v1.9 and Picard to fix paired-end mate and remove PCR duplicates. Remaining alignments in BAM format were processed using BCFtools v1.9 with following parameters "--ploidy 1" and VCFtools v0.1.17 to call genomic variation (SNPs and Indels). Resulting variations were further subjected to manual inspection to remove any false positive due to low reads coverage and misalignment of homologous regions. The illumina reads for both strains, Pacbio reads for Fn12230 and de novo genome assembly of Fn12230 are deposited in NCBI database with the accession number SRA: PRJNA632750.

Verification of SNPs between Fn 12230 and 1am. For each SNP in 1am identified by genome sequencing, primers were designed (Table 5) to amplify the SNP-containing region from Fn 12230 and 1am by PCR. The PCR amplicons were submitted for Sanger sequencing (Vendor) to verify the sequence variations.

Circular dichroism (CD) test. CD was used to evaluate the secondary structure of FadA and its mutants. One hundred microliter of 0.2 mg/ml purified FadA was analyzed by Chirascan V100 Spectrometer using a 1 mm path-length fused quartz cell. The measurements are an average of three scans for each sample, captured at a scan rate of 1 sec., bandwidth and step size of 1 nm, over a wavelength range of 190-250 nm. CD spectra were recorded and analyzed with BestSel server (see www at bestsel.elte.hu/).

Collection of dental plaque samples. This study was reviewed and approved by the Institutional Review Board of Columbia University Medical Center (IRB-AAAR7153). Subjects were recruited from patients who presented to Columbia University College of Dental Medicine. Inclusion criteria included subjects of 18 years of age or older who were in good general health or controlled common systemic conditions. Subjects with chronic periodontitis were defined as those with presence of proximal attachment loss ≥3 mm in ≥2 non-adjacent teeth. Both diseased and healthy sites (probing depth ≤3 mm, without clinical attachment loss and bleeding on probing) are present in the oral cavity. Periodontally healthy subjects were defined as those with no site with probing depth ≥3 mm, no site with attachment loss and bleeding on probing at 10% sites. Subjects who had been on antibiotics within 3 months of enrollment, were diagnosed with infectious diseases, such as HIV and hepatitis, and had history of periodontal treatment within 6 months, smoked more than 10 cigarettes per day, had uncontrolled or poorly controlled diabetes or other metabolic diseases, as well as women who were pregnant or nursing a child, were excluded. Written consent form was obtained from all the subjects before the plaque collection. Subgingival plaque samples were collected using sterilized curettes from the interproximal areas from a group of 40 patients: 20 diagnosed with chronic periodontitis and 20 periodontally healthy participants, matched for age, gender and race. From each patient with chronic periodontitis, two subgingival plaque samples were collected, with one pooled from the diseased sites (probing depth ≥7 mm, with clinical attachment loss) and another pooled from healthy sites (probing depth ≤3 mm, without clinical attachment loss and bleeding on probing).

Real-time quantitative PCR. DNA was extracted from plaque samples and the concentration was measured using NanoDrop ND 1000 spectrophotometer. Real-time quantitative PCR (qPCR) was performed in duplicates, using StepOnePlus™ (Applied Biosystems). Each 20 µl reaction was prepared with Power SYBR® Green PCR Master Mix kit according to the manufacturer's instructions (Applied Biosystems). Specific forward and reverse primers, listed in the Table 5, were used at concentration of 500 nM. PCR amplifications were performed as following: 95° C. for 10 minutes followed by 40 cycles of 95° C. for 30 seconds, 60° C. for 30 seconds, and 72° C. for 30 seconds, then 95° C. for 15 seconds and 60° C. for 1 minute, ending with a 95° C. for 15 seconds. To quantify gene copies, standard curves using plasmids carrying 16S rRNA gene or fadA gene were generated. Each experiment was performed in duplicate and repeated at least twice.

Biofilm assay. An aliquot of 50 µl 0.2 mg/ml detergent-resistant pellet, or PBS, was added into each well in a 96-well plate and incubated at 37° C. for 5 hrs. A total of 200 µl Fn 12230 (OD600 0.2), or Columbia broth alone, was added to the wells in the presence of 0, 10, and 50 µg/ml Congo Red, followed by anaerobic incubation at 37° C. for 48 or 72 hrs. The wells were then washed, and the biofilms were stained with 100 µl 0.1% crystal violet solution for 15 min. After washing, 100 µl 95% ethanol was added to each well and incubate for 15 min at room temperature, and the optical density at OD550 was measured in a microplate reader. Each experiment was performed in duplicate and repeated four times. [00194] pH tolerance assay. Fn 12230 and US1 were grown to 0.4 OD600 (log phase) or >0.8 OD600 (stationary phase), resuspended in pre-reduced PBS at pH 4.0 or 7.0, and incubated at room temperature with or without 50 µg/ml Congo Red. At 0, 1, or 2 hours, aliquots of the bacterial suspension were taken for serial dilutions and plating on blood agar plates. The plates were incubated anaerobically at 37° C. to enumerate the viable cell counts. Each experiment was performed in duplicate or triplicate and repeated 3-5 times.

Cell culture attachment assay. The assay was performed as previously described (Han et al., 2000). Briefly, DLD1 cells were seeded in 24-well plates at 1×10$^5$ cells per well and grown to 90% confluent. The bacteria were either used or washed twice with PBS or 1 mg/mL Congo Red, before adding to the monolayers at a multiplicity of infection (MOI) of 50:1 and incubated for 1 hour at 37° C. in 5% $CO_2$. Following washes with PBS, the monolayers were lysed with water, and serial dilutions of the lysates were plated onto blood agar plates to enumerate the total cell-associated bacteria. The level of attachment was expressed as the percentage of bacteria recovered following cell lysis relative to the total number of bacteria initially added. Each experiment was performed in duplicate and repeated four times. For the inhibitory binding assays, 20 µl mAb 7H7, or 50 µg FadA with or without 20 µl rabbit IgG (1 mg/ml) or OC were mixed with Fn before adding to the cells.

CRC xenograft model. Four to five-week old female NCR/NU mice were purchased from Taconic Biosciences (NY, USA). An inoculum of 5×10$^6$ HCT116 cells was injected subcutaneously and bilaterally into the mice. After 3-5 days, the following were injected into the tumors: 5×10$^6$ CFU bacterial cells washed twice with PBS or 1 mg/ml Congo Red, 4 µl (2 mg/ml) FadAc mixed with 6 µl α-amyloid OC antibody or rabbit IgG control, or 10 µl (2 mg/ml) sarkosyl resistant pellets prepared from Fn or US1 (ΔfadA) alone, or 4 µl (5 mg/ml) sarkosyl resistant pellets mixed with 6 µl rabbit IgG or OC. The tumor length and width were measured using calipers and tumor volumes were calculated using the following formula: Volume=(width)2×length/2. After the tumors were taken out, they were fixed in 4% PFA for 24 hours and embedded in paraffin for IHC as described above.

Mouse periodontitis model. This study was reviewed and approved by the Institutional Animal Care and Use Committee (IACUC) under Animal Care Protocol AC-AAAT1453 (Y2 M01). C57BL/6 mice were premedicated with prophylactic antibiotic regimen 1 week prior to bacterial inoculation. Approximately 1×10$^9$ CFU each of Fn 12230, US1, and Iam were resuspended in 2% carboxymethylcellulose (CMC). The oral cavity of 8 week-old C57BL/6 mice were prophylactically swabbed with 0.12% chlorhexidine gluconate in order to reduce endogenous bacterial flora prior to bacterial inoculation. Fn 12230, US1, and Iam resuspended in CMC were administered via oral inoculation three-four times a week for 10 weeks, with CMC alone being administered as a control. At the conclusion of the 10-week period, inoculated C57BL/6 mice were sacrificed via $CO_2$ and cervical dislocation, serum was collected by cardiac puncture, and mice were decapitated. Jaws were defleshed, maxillae were harvested, fixed in 4% paraformaldehyde (PFA) for 24 hours, and stored in 70% ethanol for prior to µCT analysis.

µCT analysis of mouse bone. Maxillae harvested from CMC alone, Fn 12230, US1, and Iam inoculated C57BL/6 mice were scanned for µCT using a Scanco vivaCT 80 System (Brüttisellen, Switzerland) using machine settings of 55 kVp, 145 µA, and 250 ms integration time. Grayscale images were reconstructed with a voxel size of 10.4 µm, smoothed using a Gaussian filter to remove noise (sigma=0.8, support=1), and threshold was set at 40% of the maximum grayscale value to isolate mineralized tissue. CEJ to alveolar crest measurements were made manually on reconstructed images using ImageJ. Measurements for each mesiobuccal, distobuccal, buccal, and palatal root, or palatal root alone, among all mice were averaged, and the standard deviation was determined. The differences between groups were examined by two-tailed t-test and p<0.05 was considered statistically significant.

Statistical analysis. The differences between groups were examined by paired t-test or one-way ANOVA. P value<0.05 was considered statistically significant.

TABLE 1

Circular dichroism analysis of FadA protein.

| Protein | Wavelength range for analysis (nm) | α helix (%) | β strand (%) |
|---|---|---|---|
| FadAc | 190-250 | 47.2 | 9.6 |
| L-9A | 190-250 | 24.4 | 21.8 |
| mFadA | 190-250 | 27.9 | 18.8 |
| L14A | 190-250 | 44.2 | 11.6 |
| S71A | 190-250 | 49.1 | 8 |

TABLE 2

SNP comparison between Fn 12230 and lam.

| | | Genome sequence | | Sanger sequence | | |
|---|---|---|---|---|---|---|
| Variation | Location (nt) | Fn 12230 | lam | Fn 12230 | lam | Notes |
| 1 | 1229082 | A | T | T | T | Not a SNP |
| 2 | 1472751 | T | C | C | C | Not a SNP |
| 3 | 1998179 | A | C | | Δ18 nt | Indel confirmed: 6-aa in-frame deletion from ORF of 4501 aa, with 62.3% identity to Fap2 from Fn 23726 |
| 4 | 2028098 | 19 × (GTCC) | 15 × (GTCC) | 19 × (GTCC) | 19 × (GTCC) | Not a SNP |
| 5 | 2139412 | A | T | A | A | Not a SNP |
| 6 | 2180734 | T | A | T | A | SNP confirmed: N284I in ORF of 845 aa; homologous to glycerol kinase |

TABLE 3

FadA homologs identified on Fn 12230.

| Gene name | CDS id | Contig | Start | End | Strand | Length | Sequence identity to FadA | Coverage of alignment to FadA |
|---|---|---|---|---|---|---|---|---|
| FadA | DOJBCGPA_00667 | Fnuc_hybrid.0 | 611715 | 612103 | + | 387 nt/ 129 aa | 100.00% | 100.00% |
| FadA 2 | DOJBCGPA_00650 | Fnuc_hybrid.0 | 590415 | 590816 | + | 402 nt/ 134 aa | 24.50% | 96.10% |
| FadA 3 | DOJBCGPA_02330 | Fnuc_hybrid.0 | 2332940 | 2333334 | + | 393 nt/ 131 aa | 25.00% | 96.10% |

TABLE 4

Bacterial strains used in this study.

| Strain name | Description | Reference |
|---|---|---|
| E. coli BL 21 (DE3)/pET21(b) | Vector control | (Xu et al, 2007) |
| E. coli BL 21 (DE3)/pYWH417-6 | Expresses recombinant FadAc | (Xu et al., 2007) |
| E. coli BL 21 (DE3)/pYWH418 | Expressed recombinant mFadA | This study |
| E. coli MC4100 | Curli-producing strain | (Evans et al, 2018) |
| E. coli MC4100 Δcsg | Curli-defective mutant | (Evans et al., 2018) |
| E. coli MC4100 ΔcsgA | Curli-defective mutant | (Evans et al., 2018) |
| Fn 12230 | Trans tracheal isolate; lab working strain; Fn subsp polymorphum | (Han et al, 2000) |
| US1 | fadA-deletion mutant of Fn 12230 | (Han et al, 2005) |
| lam | Spontaneous mutant of Fn 12230 | (Han et al., 2000) |
| Fn ATCC 23726 | Fn subsp nucleatum | ATCC |
| Fn 23726 (Δfap2) | fap2-deletion mutant of Fn 23726 | (Kaplan et al, 2009) |

TABLE 5

Primers used in this study.

| Primer name | Primer sequences (5'-3") |
|---|---|
| Bacterial 16S F | ACTCCTACGGGAGGCAGCAG (SEQ ID NO: 10) |
| Bacterial 16S R | ATTACCGCGGCTGCTGG (SEQ ID NO: 11) |
| Fn 16S F | AAGCGCGTCTAGGTGGTTATGT (SEQ ID NO: 12) |
| Fn 16S R | TGTAGTTCCGCTTACCTCTCCAG (SEQ ID NO: 13) |

TABLE 5-continued

Primers used in this study.

| Primer name | Primer sequences (5'-3") |
|---|---|
| fadA F | TAGCACAAAATGAACAAGTTTAC (SEQ ID NO: 14) |
| fadA R | ATAAAATCTTGTGTTAGCTTC (SEQ ID NO: 15) |
| SNP 1 F | CGATCTAGAATGAGTAAAAGCTTTTATAT (SEQ ID NO: 16) |
| SNP 1 R | CGACTCGAGTTATTTAGATTTATTAAGTT (SEQ ID NO: 17) |
| SNP 2 F | CGGTCTAGAATGAAAAAATCTTATATTTT (SEQ ID NO: 18) |
| SNP 2 R | CGACTCGAGTCAATTAGAGAATTTATTTT (SEQ ID NO: 19) |
| SNP 3 F | GCTCAAGAGTTGGGGGAACA (SEQ ID NO: 20) |
| SNP 3 R | TCCACCAGCATGTTGAACTGT (SEQ ID NO: 21) |
| SNP 4 F | TTGCTGTATGTCCGCCTGTT (SEQ ID NO: 22) |
| SNP 4 R | ATCGGACTTCCTGCTGAGAT (SEQ ID NO: 23) |
| SNP 5 F | AGCTCAAACTGGTGAGCCAA (SEQ ID NO: 24) |
| SNP 5 R | TCAGCCTTTGGGGCTTCTTC (SEQ ID NO: 25) |
| SNP 6 F | AAGGCAGTGAGTCAACCAGT (SEQ ID NO: 26) |
| SNP 6 R | TGCCCACCAATTAAAGTTGCAC (SEQ ID NO: 27) |

TABLE 6

Novel anti-amyloid-like FadA antibody. VH & VL1 or VH-VL2.

| | | Nucleotide sequence | Translation |
|---|---|---|---|
| VH | CDR1 | ggctacacctttactacctactgg | GYTFTTYW (SEQ ID NO: 1) |
| | CDR2 | attaatcctaacactgattatact | INPNTDYT (SEQ ID NO: 2) |
| | CDR3 | gcaagatccggttacttcggtagtaggtactactttgactac | ARSGYFGSRYYFDY (SEQ ID NO: 3) |
| VL1 | CDR1 | cagagtcttgcaaacagttatgggaacacctat | QSLANSYGNTY (SEQ ID NO: 4) |
| | CDR2 | gggatttcc | GIS (SEQ ID NO: 5) |
| | CDR3 | ttacaaggtacacatcagcctccgacg | LQGTHQPPT (SEQ ID NO: 6) |
| VL2 | CDR1 | caagacattaacaagtat | QDINKY (SEQ ID NO: 7) |
| | CDR2 | tacacatct | YTS (SEQ ID NO: 8) |
| | CDR3 | ctacagtatgattatcttctacac | LQYDYLLH (SEQ ID NO: 9) |

Data Availability

The illumina reads of Fn 12230 and the lam mutant, Pacbio reads for Fn 12230, and de novo genome assembly of Fn12230 are deposited in NCBI database with the accession number SRA: PRJNA632750.

REFERENCES

Abed J, Emgard J E, Zamir G, Faroja M, Almogy G, Grenov A, Sol A, Naor R, Pikarsky E, Atlan K A et al (2016) Fap2 Mediates *Fusobacterium nucleatum* Colorectal Adenocarcinoma Enrichment by Binding to Tumor-Expressed Gal-GalNAc. Cell Host Microbe 20: 215-225

Baym M, Kryazhimskiy S, Lieberman T D, Chung H, Desai M M, Kishony R (2015) Inexpensive multiplexed library preparation for megabase-sized genomes. PLoS One 10: e0128036

Berchowitz L E, Kabachinski G, Walker M R, Carlile T M, Gilbert W V, Schwartz T U, Amon A (2015) Regulated Formation of an Amyloid-like Translational Repressor Governs Gametogenesis. Cell 163: 406-418

Boke E, Ruer M, Wuhr M, Coughlin M, Lemaitre R, Gygi S P, Alberti S, Drechsel D, Hyman A A, Mitchison T J (2016) Amyloid-like Self-Assembly of a Cellular Compartment. Cell 166: 637-650

Bullman S, Pedamallu C S, Sicinska E, Clancy T E, Zhang X, Cai D, Neuberg D, Huang K, Guevara F, Nelson T et al (2017) Analysis of *Fusobacterium* persistence and antibiotic response in colorectal cancer. Science 358: 1443-1448

Casasanta M A, Yoo C C, Udayasuryan B, Sanders B E, Umana A, Zhang Y, Peng H, Duncan A J, Wang Y, Li L et al (2020) *Fusobacterium nucleatum* host-cell binding and invasion induces IL-8 and CXCL1 secretion that drives colorectal cancer cell migration. Science signaling 13

Castellarin M, Warren R L, Freeman J D, Dreolini L, Krzywinski M, Strauss J, Barnes R, Watson P, Allen-Vercoe E, Moore R A et al (2012) *Fusobacterium nucleatum* infection is prevalent in human colorectal carcinoma. Genome Res 22: 299-306

Cegelski L, Pinkner J S, Hammer N D, Cusumano C K, Hung C S, Chorell E, Aberg V, Walker I N, Seed P C, Almqvist F et al (2009) Small-molecule inhibitors target *Escherichia coli* amyloid biogenesis and biofilm formation. Nature chemical biology 5: 913-919

Coppenhagen-Glazer S, Sol A, Abed J, Naor R, Zhang X, Han Y W, Bachrach G (2015) Fap2 of *Fusobacterium nucleatum* is a galactose-inhibitable adhesin involved in coaggregation, cell adhesion, and preterm birth. Infect Immun 83: 1104-1113

Evans M L, Gichana E, Zhou Y, Chapman M R (2018) Bacterial Amyloids. In: Amyloid Proteins: Methods and Protocols, Sigurdsson E. M., Calero M., Gasset M. (eds.) pp. 267-288. Springer New York: New York, NY Fardini Y, Wang X, Temoin S, Nithianantham S, Lee D, Shoham M, Han Y W (2011) *Fusobacterium nucleatum* adhesin FadA binds vascular endothelial cadherin and alters endothelial integrity. Mol Microbiol 82: 1468-1480

Han Y W (2006) Laboratory maintenance of fusobacteria. Curr Protoc Microbiol Chapter 13: Unit 13A 11

Han Y W, Fardini Y, Chen C, Iacampo K G, Peraino V A, Shamonki J M, Redline R W (2010) Term stillbirth caused by oral *Fusobacterium nucleatum*. Obstet Gynecol 115: 442-445

Han Y W, Ikegami A, Rajanna C, Kawsar H I, Zhou Y, Li M, Sojar H T, Genco R J, Kuramitsu H K, Deng C X (2005) Identification and characterization of a novel adhesin unique to oral fusobacteria. J Bacteriol 187: 5330-5340

Han Y W, Shen T, Chung P, Buhimschi I A, Buhimschi C S (2009) Uncultivated bacteria as etiologic agents of intra-amniotic inflammation leading to preterm birth. J Clin Microbiol 47: 38-47

Han Y W, Shi W, Huang G T, Kinder Haake S, Park N H, Kuramitsu H, Genco R J (2000) Interactions between periodontal bacteria and human oral epithelial cells: *Fusobacterium nucleatum* adheres to and invades epithelial cells. Infect Immun 68: 3140-3146

Hsieh Y Y, Tung S Y, Pan H Y, Yen C W, Xu H W, Lin Y J, Deng Y F, Hsu W T, Wu C S, Li C (2018) Increased Abundance of *Clostridium* and *Fusobacterium* in Gastric Microbiota of Patients with Gastric Cancer in Taiwan. Scientific reports 8: 158

Ikegami A, Chung P, Han Y W (2009) Complementation of the fadA mutation in *Fusobacterium nucleatum* demonstrates that the surface-exposed adhesin promotes cellular invasion and placental colonization. Infect Immun 77: 3075-3079

Jiang B (2017) Aerobic glycolysis and high level of lactate in cancer metabolism and microenvironment. Genes Dis 4: 25-27

Kaplan C W, Ma X, Paranjpe A, Jewett A, Lux R, Kinder-Haake S, Shi W (2010) *Fusobacterium nucleatum* outer membrane proteins Fap2 and RadD induce cell death in human lymphocytes. Infect Immun 78: 4773-4778

Kayed R, Head E, Sarsoza F, Saing T, Cotman C W, Necula M, Margol L, Wu J, Breydo L, Thompson J L et al (2007) Fibril specific, conformation dependent antibodies recognize a generic epitope common to amyloid fibrils and fibrillar oligomers that is absent in prefibrillar oligomers. Molecular neurodegeneration 2: 18

Kim G W, Kim Y S, Lee S H, Park S G, Kim D H, Cho J Y, Hahm K B, Hong S P, Yoo J H (2019) Periodontitis is associated with an increased risk for proximal colorectal neoplasms. Scientific reports 9: 7528

Kostic A D, Chun E, Robertson L, Glickman J N, Gallini C A, Michaud M, Clancy T E, Chung D C, Lochhead P, Hold G L et al (2013) *Fusobacterium nucleatum* potentiates intestinal tumorigenesis and modulates the tumor-immune microenvironment. Cell Host Microbe 14: 207-215

Kostic A D, Gevers D, Pedamallu C S, Michaud M, Duke F, Earl A M, Ojesina A I, Jung J, Bass A J, Tabernero J et al (2012) Genomic analysis identifies association of *Fusobacterium* with colorectal carcinoma. Genome Res 22: 292-298

Liu Y, Baba Y, Ishimoto T, Iwatsuki M, Hiyoshi Y, Miyamoto Y, Yoshida N, Wu R, Baba H (2019) Progress in characterizing the linkage between *Fusobacterium nucleatum* and gastrointestinal cancer. Journal of gastroenterology 54: 33-41

Manson McGuire A, Cochrane K, Griggs A D, Haas B J, Abeel T, Zeng Q, Nice J B, MacDonald H, Birren B W, Berger B W et al (2014) Evolution of invasion in a diverse set of *Fusobacterium* species. mBio 5: e01864

Mima K, Nishihara R, Qian Z R, Cao Y, Sukawa Y, Nowak J A, Yang J, Dou R, Masugi Y, Song M et al (2016) *Fusobacterium nucleatum* in colorectal carcinoma tissue and patient prognosis. Gut 65: 1973-1980

Mitsuhashi K, Nosho K, Sukawa Y, Matsunaga Y, Ito M, Kurihara H, Kanno S, Igarashi H, Naito T, Adachi Y et al (2015) Association of *Fusobacterium* species in pancreatic cancer tissues with molecular features and prognosis. Oncotarget 6: 7209-7220

Nithianantham S, Xu M, Yamada M, Ikegami A, Shoham M, Han Y W (2009) Crystal structure of FadA adhesin from *Fusobacterium nucleatum* reveals a novel oligomerization motif, the leucine chain. J Biol Chem 284: 3865-3872

Ortiz P, Bissada N F, Palomo L, Han Y W, Al-Zahrani M S, Panneerselvam A, Askari A (2009) Periodontal therapy reduces the severity of active rheumatoid arthritis in patients treated with or without tumor necrosis factor inhibitors. J Periodontol 80: 535-540

Richardson M, Ren J, Rubinstein M R, Taylor J A, Friedman R A, Shen B, Han Y W (2020) Analysis of 16S rRNA genes reveals reduced Fusobacterial community diversity when translocating from saliva to GI sites. Gut Microbes 12: 1-13

Rubinstein M R, Baik J E, Lagana S M, Han R P, Raab W J, Sahoo D, Dalerba P, Wang T C, Han Y W (2019) *Fusobacterium nucleatum* promotes colorectal cancer by inducing Wnt/beta-catenin modulator Annexin A1. EMBO reports Rubinstein M R, Wang X, Liu W, Hao Y, Cai G, Han Y W (2013) *Fusobacterium nucleatum* promotes colorectal carcinogenesis by modulating E-cadherin/0-catenin signaling via its FadA adhesin. Cell Host Microbe 14: 195-206

Sanchez I, Mahlke C, Yuan J (2003) Pivotal role of oligomerization in expanded polyglutamine neurodegenerative disorders. Nature 421: 373-379

Segata N, Haake S K, Mannon P, Lemon K P, Waldron L, Gevers D, Huttenhower C, Izard J (2012) Composition of the adult digestive tract bacterial microbiome based on seven mouth surfaces, tonsils, throat and stool samples. Genome biology 13: R42

Sondheimer N, Lindquist S (2000) Rnq1: an epigenetic modifier of protein function in yeast. Molecular cell 5: 163-172

Strauss J, Kaplan G G, Beck P L, Rioux K, Panaccione R, Devinney R, Lynch T, Allen-Vercoe E (2011) Invasive potential of gut mucosa-derived *Fusobacterium nucleatum* positively correlates with IBD status of the host. Inflamm Bowel Dis 17: 1971-1978

Swidsinski A, Dorffel Y, Loening-Baucke V, Theissig F, Ruckert J C, Ismail M, Rau W A, Gaschler D, Weizenegger M, Kuhn S et al (2011) Acute appendicitis is characterised by local invasion with *Fusobacterium nucleatum/necrophorum*. Gut 60: 34-40

Tayeb-Fligelman E, Tabachnikov O, Moshe A, Goldshmidt-Tran O, Sawaya M R, Coquelle N, Colletier J P, Landau M (2017) The cytotoxic *Staphylococcus aureus* PSMalpha3 reveals a cross-alpha amyloid-like fibril. Science 355: 831-833

Temoin S, Chakaki A, Askari A, El-Halaby A, Fitzgerald S, Marcus R E, Han Y W, Bissada N F (2012a) Identification of oral bacterial DNA in synovial fluid of patients with arthritis with native and failed prosthetic joints. J Clin Rheumatol 18: 117-121

Temoin S, Wu K L, Wu V, Shoham M, Han Y W (2012b) Signal peptide of FadA adhesin from *Fusobacterium nucleatum* plays a novel structural role by modulating the filament's length and width. FEBS Lett 586: 1-6

Thomas A M, Manghi P, Asnicar F, Pasolli E, Armanini F, Zolfo M, Beghini F, Manara S, Karcher N, Pozzi C et al (2019) Metagenomic analysis of colorectal cancer datasets identifies cross-cohort microbial diagnostic signatures and a link with choline degradation. Nature medicine 25: 667-678

Tomkovich S, Dejea C M, Winglee K, Drewes J L, Chung L, Housseau F, Pope J L, Gauthier J, Sun X, Muhlbauer M et al (2019) Human colon mucosal biofilms from healthy or colon cancer hosts are carcinogenic. J Clin Invest 129: 1699-1712

Tukel C, Wilson R P, Nishimori J H, Pezeshki M, Chromy B A, Baumler A J (2009) Responses to amyloids of microbial and host origin are mediated through toll-like receptor 2. Cell Host Microbe 6: 45-53

Umana A, Sanders B E, Yoo C C, Casasanta M A, Udayasuryan B, Verbridge S S, Slade D J (2019) Utilizing Whole *Fusobacterium* Genomes To Identify, Correct, and Characterize Potential Virulence Protein Families. J Bacteriol 201

Wang X, Buhimschi C S, Temoin S, Bhandari V, Han Y W, Buhimschi I A (2013) Comparative microbial analysis of paired amniotic fluid and cord blood from pregnancies complicated by preterm birth and early-onset neonatal sepsis. PLoS One 8: e56131

Wirbel J, Pyl P T, Kartal E, Zych K, Kashani A, Milanese A, Fleck J S, Voigt A Y, Palleja A, Ponnudurai R et al (2019) Meta-analysis of fecal metagenomes reveals global microbial signatures that are specific for colorectal cancer. Nature medicine 25: 679-689

Xu M, Yamada M, Li M, Liu H, Chen S G, Han Y W (2007) FadA from *Fusobacterium nucleatum* utilizes both secreted and nonsecreted forms for functional oligomerization for attachment and invasion of host cells. J Biol Chem 282: 25000-25009

Yu T, Guo F, Yu Y, Sun T, Ma D, Han J, Qian Y, Kryczek I, Sun D, Nagarsheth N et al (2017) *Fusobacterium nucleatum* Promotes Chemoresistance to Colorectal Cancer by Modulating Autophagy. Cell 170: 548-563 e516

Evans M L, Gichana E, Zhou Y, Chapman M R (2018) Bacterial Amyloids. In: Amyloid Proteins: Methods and Protocols, Sigurdsson E. M., Calero M., Gasset M. (eds.) pp. 267-288. Springer New York: New York, NY Han Y W, Ikegami A, Rajanna C, Kawsar H I, Zhou Y, Li M, Sojar H T, Genco R J, Kuramitsu H K, Deng C X (2005) Identification and characterization of a novel adhesin unique to oral fusobacteria. J Bacteriol 187: 5330-5340

Han Y W, Shi W, Huang G T, Kinder Haake S, Park N H, Kuramitsu H, Genco R J (2000) Interactions between periodontal bacteria and human oral epithelial cells: *Fusobacterium nucleatum* adheres to and invades epithelial cells. Infect Immun 68: 3140-3146

Kaplan C W, Lux R, Haake S K, Shi W (2009) The *Fusobacterium nucleatum* outer membrane protein RadD is an arginine-inhibitable adhesin required for inter-species adherence and the structured architecture of multi-species biofilm. Mol Microbiol 71: 35-47

Xu M, Yamada M, Li M, Liu H, Chen S G, Han Y W (2007) FadA from *Fusobacterium nucleatum* utilizes both secreted and nonsecreted forms for functional oligomerization for attachment and invasion of host cells. J Biol Chem 282: 25000-25009

SEQUENCE LISTING

```
Sequence total quantity: 31
SEQ ID NO: 1           moltype = AA  length = 8
FEATURE                Location/Qualifiers
REGION                 1..8
                       note = FadA AB CDR1 Heavy Chain Protein
source                 1..8
                       mol_type = protein
                       organism = synthetic construct
SEQUENCE: 1
GYTFTTYW                                                                   8

SEQ ID NO: 2           moltype = AA  length = 8
FEATURE                Location/Qualifiers
REGION                 1..8
                       note = FadA Ab CDR Heavy Chain Protein
source                 1..8
```

```
                        mol_type = protein
                        organism = synthetic construct
SEQUENCE: 2
INPNTDYT                                                                8

SEQ ID NO: 3            moltype = AA   length = 14
FEATURE                 Location/Qualifiers
REGION                  1..14
                        note = FadA Ab CDR3 Heavy Chain Protein
source                  1..14
                        mol_type = protein
                        organism = synthetic construct
SEQUENCE: 3
ARSGYFGSRY YFDY                                                         14

SEQ ID NO: 4            moltype = AA   length = 11
FEATURE                 Location/Qualifiers
REGION                  1..11
                        note = FadA Ab CDR1 Light Chain 1 Protein
source                  1..11
                        mol_type = protein
                        organism = synthetic construct
SEQUENCE: 4
QSLANSYGNT Y                                                            11

SEQ ID NO: 5            moltype =    length =
SEQUENCE: 5
000

SEQ ID NO: 6            moltype = AA   length = 9
FEATURE                 Location/Qualifiers
REGION                  1..9
                        note = FadA Ab CDR3 Light Chain 1 Protein
source                  1..9
                        mol_type = protein
                        organism = synthetic construct
SEQUENCE: 6
LQGTHQPPT                                                               9

SEQ ID NO: 7            moltype = AA   length = 6
FEATURE                 Location/Qualifiers
REGION                  1..6
                        note = FadA Ab CDR1 Light Chain 2 Protein
source                  1..6
                        mol_type = protein
                        organism = synthetic construct
SEQUENCE: 7
QDINKY                                                                  6

SEQ ID NO: 8            moltype =    length =
SEQUENCE: 8
000

SEQ ID NO: 9            moltype = AA   length = 8
FEATURE                 Location/Qualifiers
REGION                  1..8
                        note = FadA Ab CDR3 Light Chain 2 Protein
source                  1..8
                        mol_type = protein
                        organism = synthetic construct
SEQUENCE: 9
LQYDYLLH                                                                8

SEQ ID NO: 10           moltype = DNA   length = 20
FEATURE                 Location/Qualifiers
misc_feature            1..20
                        note = Bacterial 16S forward primer
source                  1..20
                        mol_type = other DNA
                        organism = synthetic construct
SEQUENCE: 10
actcctacgg gaggcagcag                                                   20

SEQ ID NO: 11           moltype = DNA   length = 17
FEATURE                 Location/Qualifiers
misc_feature            1..17
                        note = Bacterial 16S reverse primer
source                  1..17
                        mol_type = other DNA
```

```
                         organism = synthetic construct
SEQUENCE: 11
attaccgcgg ctgctgg                                                      17

SEQ ID NO: 12            moltype = DNA  length = 22
FEATURE                  Location/Qualifiers
misc_feature             1..22
                         note = Fn 16S forward primer
source                   1..22
                         mol_type = other DNA
                         organism = synthetic construct
SEQUENCE: 12
aagcgcgtct aggtggttat gt                                                22

SEQ ID NO: 13            moltype = DNA  length = 23
FEATURE                  Location/Qualifiers
misc_feature             1..23
                         note = Fn 16S reverse primer
source                   1..23
                         mol_type = other DNA
                         organism = synthetic construct
SEQUENCE: 13
tgtagttccg cttacctctc cag                                               23

SEQ ID NO: 14            moltype = DNA  length = 23
FEATURE                  Location/Qualifiers
misc_feature             1..23
                         note = fadA gene forward primer
source                   1..23
                         mol_type = other DNA
                         organism = synthetic construct
SEQUENCE: 14
tagcacaaaa tgaacaagtt tac                                               23

SEQ ID NO: 15            moltype = DNA  length = 21
FEATURE                  Location/Qualifiers
misc_feature             1..21
                         note = fadA gene reverse primer
source                   1..21
                         mol_type = other DNA
                         organism = synthetic construct
SEQUENCE: 15
ataaaatctt gtgttagctt c                                                 21

SEQ ID NO: 16            moltype = DNA  length = 29
FEATURE                  Location/Qualifiers
misc_feature             1..29
                         note = SNP 1 forward primer
source                   1..29
                         mol_type = other DNA
                         organism = synthetic construct
SEQUENCE: 16
cgatctagaa tgagtaaaag ctttttatat                                        29

SEQ ID NO: 17            moltype = DNA  length = 29
FEATURE                  Location/Qualifiers
misc_feature             1..29
                         note = SNP 1 reverse primer
source                   1..29
                         mol_type = other DNA
                         organism = synthetic construct
SEQUENCE: 17
cgactcgagt tatttagatt tattaagtt                                         29

SEQ ID NO: 18            moltype = DNA  length = 29
FEATURE                  Location/Qualifiers
misc_feature             1..29
                         note = SNP 2 forward primer
source                   1..29
                         mol_type = other DNA
                         organism = synthetic construct
SEQUENCE: 18
cggtctagaa tgaaaaaatc ttatatttt                                         29

SEQ ID NO: 19            moltype = DNA  length = 29
FEATURE                  Location/Qualifiers
misc_feature             1..29
                         note = SNP 2 reverse primer
source                   1..29
```

|  |  |  |
|---|---|---|
| | mol_type = other DNA | |
| | organism = synthetic construct | |
| SEQUENCE: 19 | | |
| cgactcgagt caattagaga atttattttt | | 29 |
| | | |
| SEQ ID NO: 20 | moltype = DNA   length = 20 | |
| FEATURE | Location/Qualifiers | |
| misc_feature | 1..20 | |
| | note = SNP 3 forward primer | |
| source | 1..20 | |
| | mol_type = other DNA | |
| | organism = synthetic construct | |
| SEQUENCE: 20 | | |
| gctcaagagt tgggggaaca | | 20 |
| | | |
| SEQ ID NO: 21 | moltype = DNA   length = 21 | |
| FEATURE | Location/Qualifiers | |
| misc_feature | 1..21 | |
| | note = SNP 3 reverse primer | |
| source | 1..21 | |
| | mol_type = other DNA | |
| | organism = synthetic construct | |
| SEQUENCE: 21 | | |
| tccaccagca tgttgaactg t | | 21 |
| | | |
| SEQ ID NO: 22 | moltype = DNA   length = 20 | |
| FEATURE | Location/Qualifiers | |
| misc_feature | 1..20 | |
| | note = SNP 4 forward primer | |
| source | 1..20 | |
| | mol_type = other DNA | |
| | organism = synthetic construct | |
| SEQUENCE: 22 | | |
| ttgctgtatg tccgcctgtt | | 20 |
| | | |
| SEQ ID NO: 23 | moltype = DNA   length = 20 | |
| FEATURE | Location/Qualifiers | |
| misc_feature | 1..20 | |
| | note = SNP 4 reverse primer | |
| source | 1..20 | |
| | mol_type = other DNA | |
| | organism = synthetic construct | |
| SEQUENCE: 23 | | |
| atcggacttc ctgctgagat | | 20 |
| | | |
| SEQ ID NO: 24 | moltype = DNA   length = 20 | |
| FEATURE | Location/Qualifiers | |
| misc_feature | 1..20 | |
| | note = SNP 5 forward primer | |
| source | 1..20 | |
| | mol_type = other DNA | |
| | organism = synthetic construct | |
| SEQUENCE: 24 | | |
| agctcaaact ggtgagccaa | | 20 |
| | | |
| SEQ ID NO: 25 | moltype = DNA   length = 20 | |
| FEATURE | Location/Qualifiers | |
| misc_feature | 1..20 | |
| | note = SNP 5 reverse primer | |
| source | 1..20 | |
| | mol_type = other DNA | |
| | organism = synthetic construct | |
| SEQUENCE: 25 | | |
| tcagcctttg gggcttcttc | | 20 |
| | | |
| SEQ ID NO: 26 | moltype = DNA   length = 20 | |
| FEATURE | Location/Qualifiers | |
| misc_feature | 1..20 | |
| | note = SNP 6 forward primer | |
| source | 1..20 | |
| | mol_type = other DNA | |
| | organism = synthetic construct | |
| SEQUENCE: 26 | | |
| aaggcagtga gtcaaccagt | | 20 |
| | | |
| SEQ ID NO: 27 | moltype = DNA   length = 22 | |
| FEATURE | Location/Qualifiers | |
| misc_feature | 1..22 | |
| | note = SNP 6 reverse primer | |

```
source                  1..22
                        mol_type = other DNA
                        organism = synthetic construct
SEQUENCE: 27
tgcccaccaa ttaaagttgc ac                                              22

SEQ ID NO: 28           moltype = AA  length = 129
FEATURE                 Location/Qualifiers
source                  1..129
                        mol_type = protein
                        organism = Fusobacterium nucleatum
SEQUENCE: 28
MKKFLLLAVL AVSASAFAAT DAASLVGELQ ALDAEYQNLA NQEEARFNEE RAQADAARQA      60
LAQNEQVYNE LSQRAQRLQA EANTRFYKSQ YQELASKYED ALKKLEAEME QQKAVISDFE     120
KIQALRAGN                                                            129

SEQ ID NO: 29           moltype = AA  length = 129
FEATURE                 Location/Qualifiers
REGION                  1..129
                        note = FadA AB Heavy Chain Protein
VARIANT                 10
                        note = misc_feature - Xaa can be any naturally occurring
                         amino acid
VARIANT                 31..34
                        note = Any amino acid or absent
VARIANT                 60..61
                        note = Any amino acid or absent
VARIANT                 73
                        note = misc_feature - Xaa can be any naturally occurring
                         amino acid
source                  1..129
                        mol_type = protein
                        organism = synthetic construct
SEQUENCE: 29
QVQLQQSGAX ELAKPGASVK MSCKASGYTF XXXXTTYWMH WVKQRPGQGL KWIGYINPNX      60
XTDYTEYNQN FKXDKATLTA DKSSSTAYMQ LSSLTSEDSA VYYCARSGYF GSRYYFDYWG     120
QGTTLTVSS                                                            129

SEQ ID NO: 30           moltype = AA  length = 128
FEATURE                 Location/Qualifiers
REGION                  1..128
                        note = FadA Ab Light Chain 1 Protein
VARIANT                 33
                        note = Any amino acid or absent
VARIANT                 58..64
                        note = Any amino acid or absent
VARIANT                 73
                        note = misc_feature - Xaa can be any naturally occurring
                         amino acid
VARIANT                 81..82
                        note = misc_feature - Xaa can be any naturally occurring
                         amino acid
VARIANT                 110..113
                        note = Any amino acid or absent
VARIANT                 128
                        note = misc_feature - Xaa can be any naturally occurring
                         amino acid
source                  1..128
                        mol_type = protein
                        organism = synthetic construct
SEQUENCE: 30
DVVVTQTPLS LPVSFGDQVS ISCRSSQSLA NSXYGNTYLS WYLHKPGQSP QLLIYGIXXX      60
XXXXSNRFSG VPXDRFSGSS XXSGTDFTLK ISTIKPEDLG MYYCLQGTHX XXXQPPTFGG     120
GTQLEIKX                                                             128

SEQ ID NO: 31           moltype = AA  length = 128
FEATURE                 Location/Qualifiers
REGION                  1..128
                        note = FadA Ab Light Chain 2 Protein
VARIANT                 30..35
                        note = Any amino acid or absent
VARIANT                 58..64
                        note = Any amino acid or absent
VARIANT                 73
                        note = misc_feature - Xaa can be any naturally occurring
                         amino acid
VARIANT                 81..82
                        note = misc_feature - Xaa can be any naturally occurring
                         amino acid
```

-continued

```
VARIANT              109..113
                     note = Any amino acid or absent
VARIANT              128
                     note = misc_feature - Xaa can be any naturally occurring
                      amino acid
source               1..128
                     mol_type = protein
                     organism = synthetic construct
SEQUENCE: 31
DIQMTQSPSS LSASLGGKVT ITCKASQDIX XXXXXNKYIA WYQHKPGKGP SLLIHYTXXX  60
XXXXSTLQPG IPXSGFSGSG XXSGRDYSFS ISNLEPEDFA TYYCLQYDXX XXXYLLHVRR  120
GTKLEIKX                                                            128
```

The invention claimed is:

1. An antibody which binds *Fusobacterium nucleatum* amyloid-like adhesin A (Fn amyloid-like FadA), or an Fn amyloid-like FadA-binding fragment thereof, or a Fn amyloid-like FadA-binding fusion protein, comprising:

a heavy chain comprising:

CDR1 having the sequence GYTFTTYW (SEQ ID NO:1);

CDR2 having the sequence INPNTDYT (SEQ ID NO:2);

CDR3 having the sequence ARSGYFGSRYYFDY (SEQ ID NO:3);

and either a light chain comprising:

CDR1 having the sequence QSLANSYGNTY (SEQ ID NO:4);

CDR2 having the sequence GIS (SEQ ID NO:5);

CDR3 having the sequence LQGTHQPPT (SEQ ID NO:6);

or a light chain comprising:

CDR1 having the sequence QDINKY (SEQ ID NO:7);

CDR2 having the sequence YTS (SEQ ID NO:8);

CDR3 having the sequence LQYDYLLH (SEQ ID NO:9).

2. The antibody, Fn amyloid-like FadA-binding fragment thereof, or Fn amyloid-like FadA-binding fusion protein of claim 1, wherein the light chain comprises:

CDR1 having the sequence QSLANSYGNTY (SEQ ID NO:4);

CDR2 having the sequence GIS (SEQ ID NO:5); and

CDR3 having the sequence LQGTHQPPT (SEQ ID NO:6.

3. The antibody, Fn amyloid-like FadA-binding fragment, or Fn amyloid-like FadA-binding fusion protein of claim 1, comprising framework regions of a light chain and/or a heavy chain which are human framework regions or have 85% or more sequence identity therewith.

4. The antibody of claim 1, wherein the antibody is a humanized antibody.

5. The antibody or Fn amyloid-like FadA-binding fragment of claim 1, wherein the antibody or antigen-binding fragment thereof has a human sequence Fc region or has 85% or more sequence identity therewith.

6. The antibody or Fn amyloid-like FadA-binding fragment of claim 1, wherein the antibody or fragment thereof is chimeric.

7. The antibody or Fn amyloid-like FadA-binding fragment of claim 1, wherein the antibody is a monospecific antibody comprising two heavy chains of identical sequence and two light chains of identical sequence.

8. The antibody of claim 1.

9. The antibody of claim 1, which is a monoclonal antibody.

10. The antibody of claim 1, wherein the antibody is an IgG1(λ) or an IgG2(λ) or an IgG4.

11. The Fn amyloid-like FadA-binding fragment of an antibody of claim 1.

12. The Fn amyloid-like FadA-binding fragment of claim 1, which is an Fab fragment, an Fab' fragment, or an F(ab)' fragment.

13. The Fn amyloid-like FadA-binding fusion protein of claim 1, which is a single chain variable fragment (scFv).

14. A pharmaceutical composition comprising an antibody which binds Fn amyloid-like FadA, or a Fn amyloid-like FadA-binding fragment thereof, or a Fn amyloid-like FadA-binding fusion protein, of claim 1 and a carrier.

15. A nucleic acid encoding a heavy chain as set forth in claim 1.

16. A nucleic acid encoding a light chain as set forth in claim 2.

* * * * *